United States Patent [19]

Muckenfuhs et al.

[11] Patent Number: 5,092,862
[45] Date of Patent: Mar. 3, 1992

[54] ELASTIC SECUREMENT OF AN ARTICLE WITH SEGMENTS CAPABLE OF BEING ELASTICALLY SHIRRED

[75] Inventors: Delmar R. Muckenfuhs, Middletown; Steven R. Gilbert, Cincinnati, both of Ohio

[73] Assignee: The Procter & Gamble Company, Cincinnati, Ohio

[21] Appl. No.: 174,058

[22] Filed: Mar. 23, 1988

[51] Int. Cl.⁵ .................. A61F 13/56; A61F 13/58; A61F 13/62
[52] U.S. Cl. ....................... 604/385.2; 604/385.1; 604/386; 604/389
[58] Field of Search ............ 604/389, 386, 390, 385.1, 604/385.2

[56] References Cited

U.S. PATENT DOCUMENTS 2,834,347  5/1958  Connally .......................... 604/389
3,620,896 11/1971  Glasgow .......................... 161/123

(List continued on next page.)

FOREIGN PATENT DOCUMENTS 0235815   9/1987  European Pat. Off. .
0236032   9/1987  European Pat. Off. .
0242175  10/1987  European Pat. Off. ...... 604/385.2 X
0211197   2/1987  France .
1324591   7/1973  United Kingdom .
1389201   4/1975  United Kingdom .
2056910   3/1981  United Kingdom .
2160473  12/1985  United Kingdom .

Primary Examiner—David J. Isabella
Assistant Examiner—David H. Willse
Attorney, Agent, or Firm—E. Kelly Linman; John V. Gorman; Richard C. Witte

[57] ABSTRACT

An article having a pliable portion which is to be elastically secured about the periphery of a member having a substantially predetermined cross-section by means of an elasticized fastening system. The pliable portion of the article has a first end portion and a second end portion located at opposite ends of the encircling portion of the article. The first end portion includes an elasticized fastening system having at least one segment which is capable of being elastically shirred along at least a portion of its length. The shirrable portion of the segment comprises an elastomeric member which, prior to the securement of the first and second end portions of the article to one another, is maintained in a prestretched and tensioned condition in the desired direction of shirring. The opposed ends of the shirrable segment in the article are interconnected to one another through the prestretched and tensioned elastomeric member. The prestretched and tensioned elastomeric member is maintained in tension by securing it in fixed relation to at least one rigidifying member to form a composite structure which is strong enough to resist collapse in a direction parallel to the tensile forces acting upon the prestretched and tensioned elastomeric member. In a particularly preferred embodiment, the rigidifying member has a fixed portion permanently secured to the first end portion of the article and a releasable portion which can be separated from the first end portion of the article. The releasable portion of the rigidifying member preferably includes means for securing it to the second end portion of the article, and the act of affixing the releasable portion of the rigidifying member to the second end portion of the article automatically releases the tension in the prestretched elastomeric member. Elasticized fastening systems of the present invention can be produced at high speed from continuous webs and cut into discrete segments which are transferred onto a continuously moving web at predetermined points along its length, all while the elastomeric member is maintained in its prestretched and tensioned condition by the rigidifying member. In a particularly preferred embodiment, the elastomeric member is prestretched in the cross-machine direction so as to cause shirring of the articles in a direction substantially perpendicular to the direction of web travel when the rigidifying member is separated from the prestretched and tensioned elastomeric member.

33 Claims, 16 Drawing Sheets

U.S. PATENT DOCUMENTS

| | | | |
|---|---|---|---|
| 3,639,917 | 2/1972 | Althouse | 2/270 |
| 3,694,815 | 10/1972 | Burger | 2/224 A |
| 3,758,363 | 9/1973 | Frick | 156/383 |
| 3,800,796 | 4/1974 | Jacob | 128/284 |
| 3,819,401 | 6/1974 | Massengale et al. | 156/85 |
| 3,848,594 | 11/1974 | Buell | 128/284 |
| 3,912,565 | 10/1975 | Koch et al. | 156/85 |
| 3,920,018 | 11/1975 | Schaar | 128/287 |
| 3,921,221 | 11/1975 | Zoephel | 2/51 |
| 3,930,503 | 1/1976 | Tritsch | 604/385.2 |
| 3,946,480 | 3/1976 | Dienes | 29/235 |
| 4,023,571 | 5/1977 | Comerford et al. | 128/290 P |
| 4,036,233 | 7/1977 | Kozak | 128/287 |
| 4,040,124 | 8/1977 | Zoephel | 2/51 |
| 4,041,949 | 8/1977 | Kozak | 128/287 |
| 4,050,462 | 9/1977 | Woon et al. | 128/287 |
| 4,051,853 | 10/1977 | Egan, Jr. | 128/287 |
| 4,063,559 | 12/1977 | Tritsch | 128/287 |
| 4,074,716 | 2/1978 | Schaar | 128/287 |
| 4,081,301 | 3/1978 | Buell | 156/164 |
| 4,090,516 | 5/1978 | Schaar | 128/287 |
| 4,126,238 | 11/1978 | Rausing | 215/1 C |
| 4,158,363 | 6/1979 | Schaar | 128/287 |
| 4,209,016 | 6/1980 | Schaar | 128/287 |
| 4,246,900 | 1/1981 | Schroder | 128/287 |
| 4,259,220 | 3/1981 | Bunnelle et al. | 260/27 BB |
| 4,300,562 | 11/1981 | Pieniak | 128/287 |
| 4,326,904 | 4/1982 | Eckert et al. | 156/85 |
| 4,338,970 | 7/1982 | Krackeler et al. | 138/141 |
| 4,352,355 | 10/1982 | Mesek et al. | 128/287 |
| 4,381,781 | 5/1983 | Sciaraffa et al. | 604/372 |
| 4,388,075 | 6/1983 | Mesek et al. | 604/385 |
| 4,389,212 | 6/1983 | Tritsch | 604/389 |
| 4,392,898 | 7/1983 | Pithouse et al. | 156/85 |
| 4,407,284 | 10/1983 | Pieniak | 604/385 |
| 4,425,390 | 1/1984 | Changani et al. | 428/43 |
| 4,447,240 | 5/1984 | Ito et al. | 604/385 |
| 4,450,026 | 5/1984 | Pieniak et al. | 156/164 |
| 4,486,366 | 12/1984 | Reddy | 264/25 |
| 4,507,163 | 3/1985 | Menard | 156/164 |
| 4,525,407 | 6/1985 | Ness | 428/138 |
| 4,527,990 | 7/1985 | Sigl | 604/385 A |
| 4,543,099 | 9/1985 | Bunnelle et al. | 604/385 A |
| 4,547,243 | 10/1985 | Brody | 156/164 |
| 4,552,795 | 11/1985 | Hansen et al. | 428/110 |
| 4,556,596 | 12/1985 | Meuli | 428/152 |
| 4,573,991 | 3/1986 | Pieniak et al. | 604/385 A |
| 4,578,133 | 3/1986 | Oshefsky et al. | 156/164 |
| 4,585,447 | 4/1986 | Karami | 604/385 A |
| 4,585,607 | 4/1986 | Krackeler et al. | 264/229 |
| 4,639,949 | 2/1987 | Ales et al. | 2/400 |
| 4,640,859 | 2/1987 | Hansen et al. | 428/105 |
| 4,643,729 | 2/1987 | Laplanche | 604/389 |
| 4,670,012 | 6/1987 | Johnson | 604/390 |
| 4,675,016 | 6/1987 | Meuli et al. | 604/385 A |
| 4,710,187 | 12/1987 | Boland et al. | 604/385 A |
| 4,710,189 | 12/1987 | Lash | 604/385 A |
| 4,726,807 | 2/1988 | Young et al. | 604/385 A |
| 4,795,456 | 1/1989 | Borgers et al. | 604/390 |
| 4,857,067 | 8/1989 | Wood et al. | 604/389 |
| 4,908,247 | 3/1990 | Baird et al. | 428/34.9 |

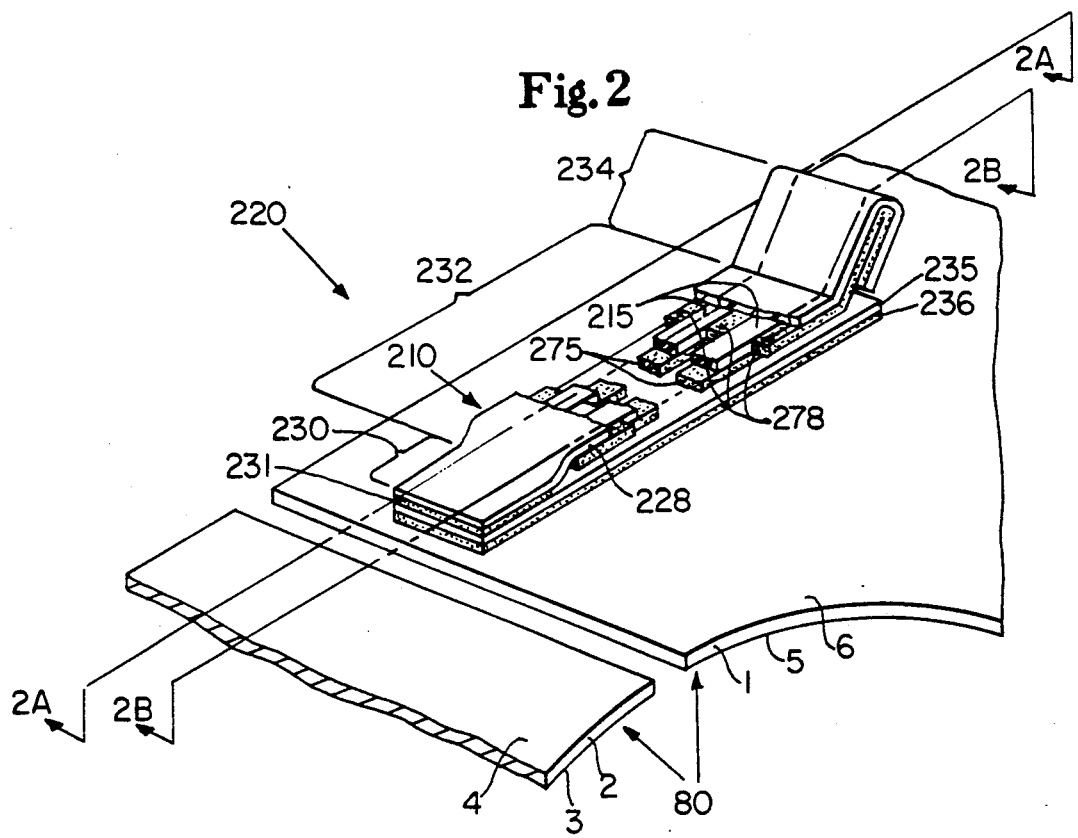
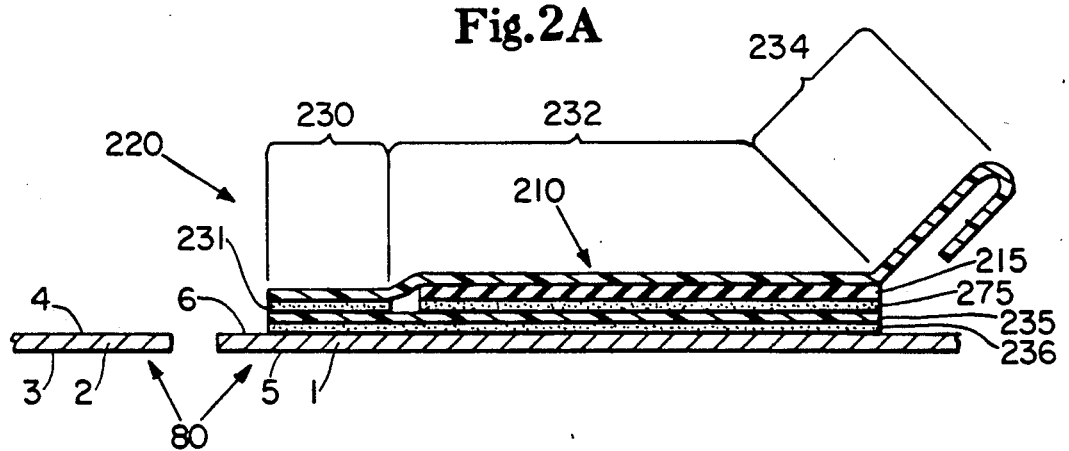

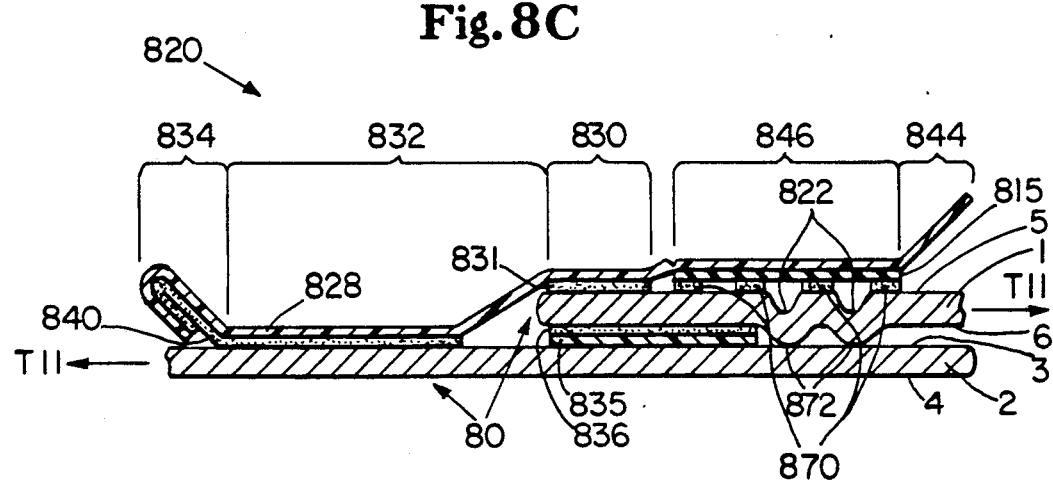
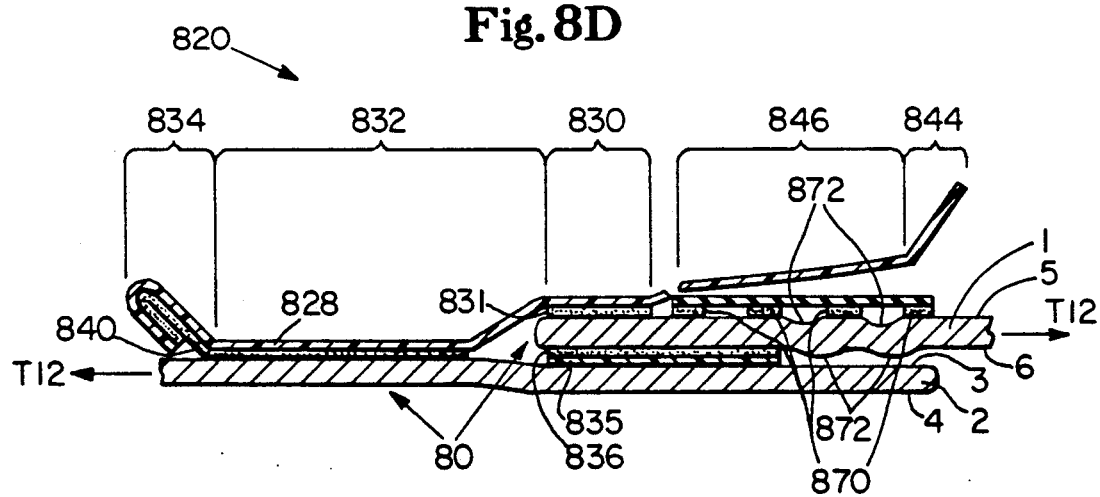

5,092,862

ELASTIC SECUREMENT OF AN ARTICLE WITH SEGMENTS CAPABLE OF BEING ELASTICALLY SHIRRED

TECHNICAL FIELD

The present invention relates to an article having a pliable portion which is to be elastically secured about the periphery of a member having a substantially predetermined cross-section.

The present invention has further relation to such an article having a pliable portion including an elasticized fastening system.

The present invention has further relation to such a system wherein the first end portion of the article includes at least one segment which is capable of being elastically shirred along at least a portion of its length, the shirrable portion of the segment preferably comprising an elastomeric member which, prior to the securement of the first and second end portions of the article to one another, is maintained in a prestretched and tensioned condition in the desired direction of shirring by at least one rigidifying member.

In a preferred embodiment, the present invention has relation to such a system wherein the rigidifying member has a fixed portion permanently secured to the first end portion of the article and a releasable portion which can be separated from the first end portion of the article, said releasable portion of the rigidifying member further including means for securing it to the second end portion of the article.

The present invention has further relation to such a system wherein separating the releasable portion of the rigidifying member from the first end portion of the article releases the tensile forces in the prestretched and tensioned elastomeric member to produce a degree of shirring in the first end portion of the article in the direction of prestretching of the elastomeric member.

In a particularly preferred embodiment, the present invention has relation to a disposable diaper having opposed waistband portions which are to be elastically secured about the periphery of an infant's waist, the opposed ends of said waistband each including such an elasticized fastening system.

In yet another preferred embodiment, the present invention relates to method and apparatus for producing such elasticized fastening systems at high speed from continuous webs and thereafter applying discrete segments cut from the composite web thus formed onto a continuously moving web of interconnected articles at predetermined locations along the length of the web, all while the elastomeric members in said fastening systems are maintained in a prestretched and tensioned condition.

In another preferred embodiment, the present invention relates to such method and apparatus, wherein a prestretched and tensioned elastomeric member is secured in fixed relation to a rigidifying member during the application process, but thereafter automatically undergoes movement relative to the rigidifying member to gather the article to which it is affixed subsequent to the manufacturing operation.

In still another preferred embodiment, the present invention relates to method and apparatus for producing and applying such elasticized fastening systems which are capable of shirring the articles to which they are affixed in a direction substantially perpendicular to the direction of web travel when the rigidifying members are separated from the prestretched and tensioned elastomeric members.

BACKGROUND OF THE INVENTION

The use of elastomeric materials to improve fit is well known in many different arts. Prior art articles, such as garments, both durable and disposable, have incorporated bands of stretched elastomeric material in waistbands, legbands, anklebands, cuffbands, headbands and the like.

One common class of elastomeric materials used in these applications is comprised of "live" elastics, such as natural rubber. These are typically secured to the article to be elasticized while they are held in a tensioned condition, or the article must be foreshortened while the end points of the elastomeric member are secured thereto. The former operation, i.e., applying the elastics in a tensioned condition, is often difficult to do, particularly at high speed. It is even more difficult when the desired direction of elasticity is substantially perpendicular to the direction of article or web travel. While the latter approach, i.e., foreshortening the article and securing the end points of the untensioned elastics thereto, does permit the elastomeric material to be applied in a substantially untensioned condition, it is generally ineffective to produce uniform shirring or gathering of the article due to the fact that only the end points of the elastic member are secured thereto.

Another prior art approach which has been developed over the years relates to the use of heat shrinkable elastomeric materials. Such materials can be applied in a substantially untensioned state and thereafter caused to shrink in a predetermined direction by the application of an external stimulus, such as heat. While this approach has been utilized with reasonable success in producing articles such as disposable diapers having elasticized waistbands, heat shrinkable elastomeric materials are generally more expensive than "live" elastomeric materials. In addition, the amount of elastic recovery obtainable with such materials is generally less than for prestretched "live" elastomeric materials. Finally, the post application stimulus is often difficult to apply in a reliable fashion, and the need to apply the post application stimulus may impose restraints on the types of materials which can be employed adjacent the heat shrinkable elastomeric material and/or the methods of assembly used to construct the article.

More recently, an elastically shirrable segment comprising a "live" elastomeric member which is maintained in a prestretched and tensioned condition in the desired direction of article shirring by a rigidifying member has been developed. This elastically shirrable segment overcomes many of the difficulties associated with the aforementioned prior art elasticization processes. Details of the elastically shirrable segment are fully described in commonly assigned European Patent Application No. 0,242,175 filed in the names of James Clark Baird, Delmar Ray Muckenfuhs, Thurman J. Koger II, and Milton Daniel Spahni, and entitled "Article Including Segment Which Is Elastically Shirrable After Manufacture", said application being published on Oct. 21, 1987, and hereby incorporated herein by reference.

The aforementioned commonly assigned European Patent Application of Baird et al. discloses how the aforementioned elastically shirrable segments can be attached to an article to provide shirring in whatever direction is desired upon effecting separation of or relative movement between the rigidifying member and the prestretched and tensioned elastomeric member.

It is an object of the present invention to provide an elasticized fastening system incorporating an elastically shirrable segment of the type generally disclosed in the aforementioned commonly assigned European Patent Application of Baird et al.

It is a further object of the present invention to provide such a fastening system wherein tension is automatically released in the prestretched and tensioned elastomeric member when the end user applies the article in question to an object of substantially predetermined cross-section.

It is another object of the present invention to provide such a fastening system, wherein the rigidifying member includes a releasable portion which not only maintains the prestretched elastomeric member in tension until the article is applied by the end user, but which also may be used to secure the first and second end portions of the article to one another.

It is still another object of the present invention to provide high speed method and apparatus for continuously assembling and applying such elasticized fastening systems which are capable of shirring the article to which they are affixed in a direction substantially perpendicular to the direction in which the web travels during the article manufacturing process whenever tension in the prestretched and tensioned elastomeric member is released.

DISCLOSURE OF THE INVENTION

The present invention has relation to an article having a pliable portion which is to be elastically secured about the periphery of a member having a substantially predetermined cross-section. The pliable portion of the article has a first end portion and a second end portion located at opposite ends of the encircling portion of the article. The first end portion includes at least one segment which is capable of being elastically shirred along at least a portion of its length. The shirrable portion of the segment comprises an elastomeric member which, prior to the securement of the first and second end portions of the article to one another, is maintained in a prestretched and tensioned condition in the desired direction of shirring. The opposed ends of the shirrable segment in the article are interconnected to one another through the prestretched and tensioned elastomeric member. The prestretched and tensioned elastomeric member is maintained in tension by securing it in fixed relation to at least one rigidifying member to form a composite structure which is strong enough to resist collapse in a direction parallel to the tensile forces acting upon the prestretched and tensioned elastomeric member. In a particularly preferred embodiment, the rigidifying member has a fixed portion permanently secured to the first end portion of the article and a releasable portion which can be separated from the first end portion of the article. The releasable portion of the rigidifying member further includes means for securing it to the second end portion of the article.

Separating the releasable portion of the rigidifying member from the first end portion of the article releases the tensile forces in the prestretched and tensioned elastomeric member to produce a degree of shirring in the first end portion of the article in the direction of prestretching of the elastomeric member. The degree of shirring in the secured article is inversely proportional to the amount of tension applied to the encircling portion of the article when the first and second end portions are secured to one another.

In a particularly preferred embodiment, the article comprises a disposable diaper having opposed waistband portions which are to be elastically secured about the periphery of an infant's waist. A prestretched and tensioned elastomeric member can be applied to each of the opposing ends of either the front or the back waistband portion of the diaper without significantly adding to the complexity of a conventional non-elasticized tape tab application system. The ability to use the same basic application system is made possible by virtue of the fact that the elastomeric member used in fastening systems of the present invention is maintained in its prestretched and tensioned condition by the rigidifying member during the application process. Accordingly, fastening systems of the present invention can be fabricated as a composite roll stock in which the elastomeric member is prestretched and tensioned in the cross-machine direction, i.e., perpendicular to the direction of travel of the moving diaper web. The roll stock may be fed continuously in the machine direction along with the moving diaper web, and discrete segments of the roll stock may be cut from the roll and applied to the web at predetermined points along its length, preferably predetermined points corresponding to the waistband portion of the diapers comprising the web. When the discrete segments comprising the fasteners are activated to apply the diaper waistband to the wearer, the tension in the prestretched elastomeric members is released to shirr the waistband end portions of the diapers in the cross-machine direction.

In a particularly preferred embodiment, the releasable portion of the rigidifying member comprises a pressure sensitive adhesive tape which, when separated from the first end portion of the article to which its fixed portion is permanently secured, releases the tensile forces in the prestretched elastomeric member to produce a degree of shirring in the first end portion of the article in the direction of prestretching of the elastomeric member. In the case of an article comprising a disposable diaper, the degree of shirring remaining in the waistband portion of the diaper once the opposing waistband portions of the diaper have been secured to one another is inversely proportional to the degree of tension applied to the waistband when the last rigidifying member is secured in position so that the diaper waistband completely encircles the infant's waist.

If desired, similar fastening systems of the present invention can be applied to the opposing legband portions of the diaper such that each legband can be elastically secured about a leg of the infant, substantially independent of the degree of tension applied to the opposing waistband portions of the diaper. Thus, fastening systems of the present invention permit the user to independently select the optimum degree of tension desired to accomplish a particular result without having to compromise on the desired degree of tension in a neighboring portion of the same article.

In addition, articles of the present invention are provided with noticeable elasticity immediately adjacent the area of securement. This not only improves the ability of the person applying the garment or other article to accurately control the degree of tension when securing the opposing end portions of the garment or other article to one another, but greatly enhances the user perception that the article is truly elastically secured, e.g., as about the periphery of the waist or the legs of an infant.

In many embodiments of the present invention, release of tension in the prestretched and tensioned elastomeric member or members employed in articles of the present invention is performed entirely by the end user of the product as the article is being placed in service.

However, the present invention may also be practiced to advantage by applying the prestretched and tensioned elastomeric member or members to the article while the elastomeric member is secured in fixed relation to a rigidifying member and thereafter separating all or a portion of the rigidifying member from the prestretched and tensioned elastomeric member to elasticize all or a portion of the end portion of the article before it leaves the manufacturer's plant. In the latter case, the rigidifying member can comprise either a disposable portion of the composite structure which is stripped off and discarded or a permanent portion of the article manufacturing apparatus, such as a continuous belt which travels with the moving web of articles and comprises a temporary rigidifying member for the composite structure during the composite structure application process.

In still other embodiments of the present invention the securement means employed between the rigidifying member and the prestretched and tensioned elastomeric member may be one which allows a gradual release of tension in the prestretched elastomeric member over time. These embodiments permit application of a composite structure of the present invention to an article in an untensioned state, followed by a gradual release of tension in the prestretched elastomeric member after the attachment process has been completed. This permits the article to achieve an elastically shirred configuration before it reaches the end user. In a particularly preferred embodiment the securement means can comprise an adhesive exhibiting a high degree of creep.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 2 is a simplified perspective view of the first and second end portions of another article of the present invention, said article being somewhat similar to that shown in FIG. 1;

FIG. 2A is an instantaneous cross-sectional view of the article of FIG. 2 taken along section line 2A—2A of FIG. 2;

FIG. 8C is a cross-sectional illustration of the article shown in FIG. 8 after its first and second end portions have been secured to one another in overlapping relation while subject to a degree of tension, $T_{11}$, which is not only much, much greater than the degree of tension, $T_{10}$, shown in FIG. 8B, but also greater than the degree of tension initially present in the prestretched elastomeric member, said illustration depicting the condition which would exist prior to separation of the rigidifying member from the prestretched and tensioned elastomeric member;

FIG. 8D is a cross-sectional illustration of the article shown in FIG. 8C after the rigidifying member has been separated from the prestretched and tensioned elastomeric member, permitting the pregathered portion of the first end portion of the article to expand in the direction of applied tension and thereby reduce the degree of tension present in the opposed end portions of the article to a new level $T_{12}$, which is lower than the former level $T_{11}$;

DETAILED DESCRIPTION OF THE INVENTION

Figure 1:
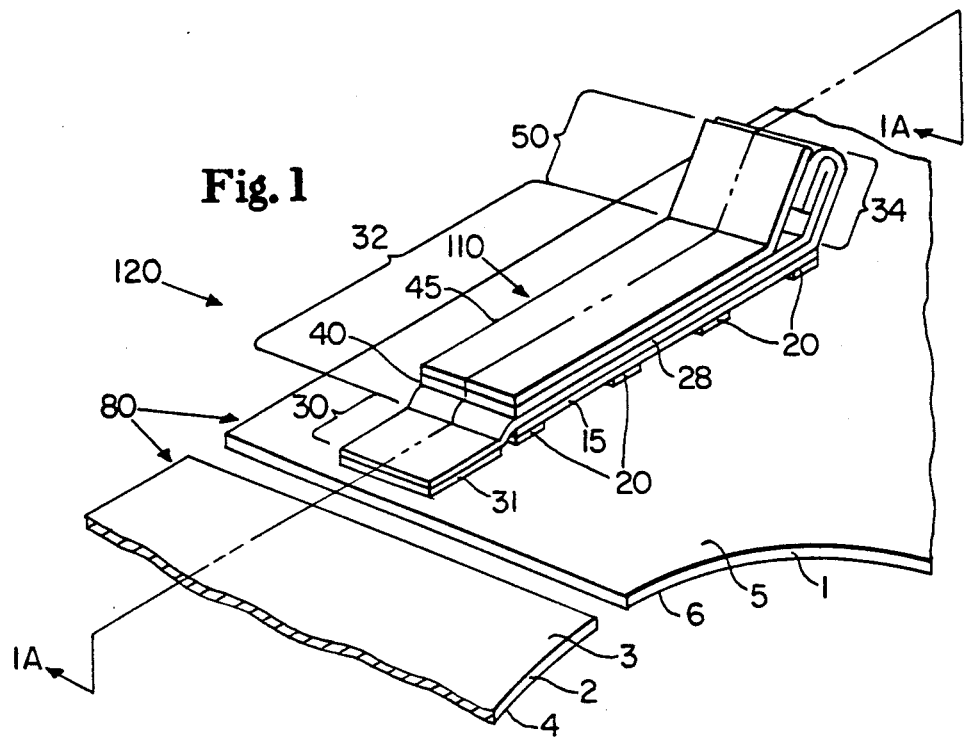
FIG. 1 is a simplified perspective illustration of a first embodiment of an article of the present invention prior to elastically securing the first and second end portions of the article to one another.

Articles having a pliable portion which is to be elastically secured about the periphery of a member of substantially predetermined cross-section may be formed in many different configurations using a variety of materials and methods of manufacture. Exemplary embodiments utilizing differing materials of construction, differing configurations and differing methods of construction will be disclosed herein for purposes of illustration only.

As a preferred environment of use, the article disclosed in the Drawing Figures and discussed in detail in the following Examples takes the form of a disposable absorbent bandage, such as a disposable diaper, having opposed waistband portions which are to be elastically interconnected to one another about the waist of the wearer. In another disclosed embodiment, the opposed portions of the diaper also form elasticized legbands about the wearer's legs utilizing a fastening system comprising a preferred embodiment of the present invention.

Because articles of the present invention are provided with noticeable elasticity immediately adjacent the area of securement, the ability of the person applying the garment or other article to accurately control the degree of tension when securing the end portions of the garment to one another is greatly enhanced. In addition, the presence of the elasticity immediately adjacent the area of securement enhances the user's perception that the article is truly elastically secured, e.g., as about the periphery of the waist and/or the legs of an infant.

While the disclosed embodiments are cast in the environment of a disposable diaper, various changes and modifications to the exemplary embodiments can be made without departing from the spirit and scope of the invention. Accordingly, these exemplary embodiments are not intended to limit the present invention, as described in the appended claims.

Materials of Construction

Composite elastically shirrable laminate structures employed on pliable articles of the present invention are generally disclosed in commonly assigned European Patent Application No. 0,242,175 filed in the names of James Clark Baird, Delmar Ray Muckenfuhs, Thurman J. Koger II, and Milton Daniel Spahni, entitled "Article Including Segment Which is Elastically Shirrable After Manufacture" and published on Oct. 21, 1987, said European Patent Application being hereby incorporated herein by reference. They are typically comprised of up to three material types. These are the elastomeric material, the rigidifying material, and an optional intermediate material such as an adhesive which may be used to secure the elastomeric material in fixed relation to the rigidifying material(s). These three types of materials are discussed separately hereinafter.

The Elastomeric Material

Preferably, the elastomeric material is a material that can undergo high levels of reversible strain. Elastomers that can be stretched to two or more times their original length and then recover to their original length once the stretching force is removed are particularly useful for the purpose of creating garment shirring. However, elastomers that cannot be reversibly stretched as far may find utility in some applications. Even elastomers which exhibit a degree of irreversible stretch may be utilized, depending upon the particular application.

Elastomers that will maintain a fixed tension when they are stretched and held for long periods of time (perhaps a year or more) are particularly preferred in situations where long periods of time may pass between the manufacture and use of the elastically shirrable article. Generally these preferred materials are comprised of thermoset rubbers, such as synthetic and natural rubbers. Silicone rubber is a particularly preferred material. Urethane based elastomers may also be used, as could natural or synthetic foam elastomers. Elastomers that will not maintain tension for a long period of time will have more limited utility in practicing the present invention. Their principal use would be in applications where the elastic is to be activated soon after lamination of the composite structure is complete (such as activation on line in a manufacturing plant) or in applications where variable and limited elastic recovery is acceptable. Elastomers that will not maintain tension for extended periods of time are generally comprised of thermoplastics, such as ethylene vinyl acetate copolymer.

The Rigidifying Material

The term "rigid", for the purpose of this invention, is a relative term. It means that the rigidifying material will not foreshorten enough to allow the compressive forces exerted by the stretched elastomer to return the stretched elastomer to its original untensioned length. That is, it is relatively inelastic when compared to the elasticity of the elastomeric component in a given laminate composite structure. Materials such as polypropylene, glycol modified [poly] ethylene terephthalate (commonly referred to as PET-G), polystyrene, blends of polystyrene and polyethylene, polyethylene laminated to paper, and surlyn are particularly preferred as a rigidifying component in articles of the present invention. These materials all have very different moduli of elasticity from one another, but used appropriately (the right thicknesses, relative material widths, elastic pretension, etc.) they all can work acceptably as a rigidifying member in articles of the present invention. The rigidifying material could also be comprised of a laminate comprising multiple layers, each serving a separate function, e.g., one of the layers could comprise a release surface or an adhesive surface and another of the layers could impart rigidity.

The rigidifying member may also be brittle or not. The decision to choose a brittle material over a ductile material depends upon the method of elastic activation desired. If it is desirable to activate the elastic by wiggling the composite to cause cracks and delamination in the rigid layer or layers, then a material brittle at the temperature of use is preferred. If however, the elastic is activated by stripping or peeling off the rigid layer from the composite structure, then a more ductile rigidifying material is preferred.

In yet another embodiment of the present invention, the rigidifying member or layer could be a durable material like steel. For example, it could be a permanent component of a machine that applies the prestretched and tensioned elastic to the garment. In this case, the elastic would be stretched and temporarily adhered to a permanent rigid layer such as an endless, flexible steel conveyor band. The resultant laminate comprising the steel conveyor band having the prestretched and tensioned elastomeric member adhered thereto would then be brought into contact with the garment or other article to be elasticized and the elastomeric member would be affixed to the article. Finally, the permanent rigidifying layer would be stripped away leaving the prestretched and tensioned elastomeric member adhered to the article as the article moved downstream. Such a method may be particularly useful for attaching stretched elastic legbands oriented generally in the machine direction to a web of disposable diapers which is also moving continuously in the machine direction. Such a method may also be of use in situations where the manufacturer desires to apply an elastomeric member which has been prestretched and tensioned in the cross-machine direction to a web moving continuously in the machine direction. Stripping away of the rigidifying layer after the elastomeric member has been applied to the continuously moving web releases the tension in the prestretched elastomeric member, causing the web and the articles cut therefrom to shirr in the cross-machine direction.

A rigidifying member of the present invention may have many different material configurations. For instance, it could be a flat film, an embossed flat film, a nonwoven fabric, a hollow tube, a rigid foam, a scrim, a laminate of several materials or a molded shape. The materials could have a wide range of thickness, depending upon the tension in the prestretched elastomeric member, and could even be variable in thickness throughout the width and/or length of the composite structure. The rigidifying member or members could also be an integral component of the article to be elasticized rather than an independent element.

The Optional Intermediate Material

The use of an intermediate material to secure the elastomeric member and the rigidifying member to one another is optional in constructing elastically shirrable segments which are to be affixed to articles of the present invention. As will also be pointed out in subsequent sections of this specification, it is not always necessary for the rigidifying members to be secured along their length directly to the prestretched elastomeric member. In some instances, an additional material could be permanently laminated to the rigidifying member, to the elastomeric member or both, to facilitate the joinder process between the elastomer and rigidifying members. In some instances, the prestretched and tensioned elastomeric member and the rigidifying member could even be secured to opposite surfaces of the article to be elasticized rather than directly to one another, e.g., as on opposite surfaces of a disposable diaper waistband.

In those situations where an intermediate material is employed intermediate the prestretched and tensioned elastomeric member and the rigidifying member, it most typically comprises an adhesive. In this capacity, it serves to bond the prestretched and tensioned elastomer to the rigidifying member. This is especially valuable where a natural heat seal bond between the prestretched elastomer and the rigidifying layer is either too strong or too weak. In this case, the adhesive must be selected so as to give the right adhesive forces and so as not to detract from the function of the composite structure.

The optional intermediate material may also comprise more than just an adhesive. It may have considerable bulk relative to the prestretched elastomer and/or rigidifying layer(s). One such example of a composite structure of the present invention could comprise a multiplicity of prestretched elastomeric strands running parallel to a multiplicity of rigidifying strands, both materials enveloped by a matrix comprised of a third material, such as a foam. In this embodiment, the foam must exhibit sufficient adhesive and mechanical strength to hold the composite structure together under the tension of the prestretched elastomeric strands, but be weak enough to collapse with the elastomer when the rigidifying strands are broken or separated from the composite structure. This type of structure may have particular utility as a replacement for durable garment elastic fastening systems.

In many embodiments of the present invention, an intermediate material is not necessary. However, when the optional intermediate material is not present, it is still a requirement that the prestretched elastomeric member and the rigidifying member be secured in fixed relation to one another so as to form a composite structure which is strong enough to resist collapse in a direction parallel to the tensile forces acting upon the prestretched elastomeric member prior to mechanical manipulation of the composite structure. Methods for securing the prestretched elastomeric member and the rigidifying member directly to one another without use of an intermediate material include heat sealing, solvent bonding (e.g., as by placing a solvent for one or both materials between the layers and then driving off the solvent), solution casting one layer onto the other, and mechanical interlocking.

Mechanical interlocking can usually be effected by subjecting a prestretched and tensioned elastomeric member having a degree of surface roughness and a heat softenable rigidifying member to heat and pressure while they are in contact with one another. The heat and pressure causes the rigidifying member to conform to the surface roughness of the prestretched elastomeric member so that upon cooling, the rigidifying member and the prestretched elastomeric member are mechanically interlocked with one another. This particularly desirable interlock has high shear strength, but low peel strength.

Bonds made without the optional intermediate layer are preferably strong enough to hold the prestretched elastomer in its full, outstretched condition before activation, yet weak enough to fail upon whatever form of activation is desired, preferably mechanical manipulation, such as stripping of the rigidifying member from the composite structure.

In still another embodiment of the present invention, the prestretched elastomeric member and the rigidifying member need not be secured to one another along their length. In simplest terms, this embodiment could comprise a tubular member having a prestretched and tensioned elastomeric member extending through the interior of the tubular member and secured at its opposite ends. In this embodiment, the tubular member must provide sufficient strength to resist the tensile forces acting upon the prestretched elastomeric member until such time as mechanical manipulation of the composite structure destroys the compression resistance of the tubular member and allows relative movement between the prestretched elastomeric member and the tubular member.

In still another embodiment of the present invention, a prestretched elastomeric member could be tightly encapsulated between a pair of polymeric webs which are secured to one another with only its opposing ends secured either directly to the webs or in some other way restrained from retracting into the tunnel formed between the webs, e.g., as by knotting the opposed ends of the stretched elastomeric member. So long as the polymeric webs are secured in intimate relation to the prestretched elastomeric member, the composite structure will resist collapse due to the tensile forces acting upon the prestretched elastomer. However, upon mechanical manipulation of the composite structure, the webs are caused to separate from the prestretched elastomeric member, thereby releasing the tension in the mechanically manipulated portions of the composite structure and shirring the webs in the mechanically manipulated portions of the structure.

In still another embodiment of the present invention, an elastomeric member could be prestretched and thereafter restrained from retracting in the direction of stretching by preventing the elastomeric member from expanding in any direction perpendicular to the direction of prestretching. This is easily understood by thinking of the elastomeric member in terms of its volume, i.e., the product of its length, width, and height dimensions. When the length of an elastomeric material is increased by stretching, its height and/or width is reduced generally in accordance with Poisson's Ratio as it relates to the conservation of volume. By preventing the height and width dimensions of the elongated elastomeric member from expanding, the length of the elastomeric volume will be maintained without any longitudinally aligned forces being applied to prevent it from recovering to its original length. This expanded state will remain stable until such time as the height and/or width dimensions are allowed to expand by removing their respective restraining members. In this embodiment of the present invention, there is no need for a bond between the encapsulating restraint member and the stretched elastomeric member to hold the elastomeric material in its expanded state, since the encapsulating restraint member exerts a compressive force on the elastomeric material. This compressive force which is exerted in a direction perpendicular to the desired direction of shirring, is sufficient to prevent the elastomeric material from expanding in a direction perpendicular to the desired direction of shirring until such time as the elastically shirrable segment is mechanically manipulated or acted upon, i.e., until such time as the encapsulating restraint member is either removed or at least ruptured, so as to release the compressive force. Removal of the compressive force instantaneously restores the tensile force in a direction parallel to the length of the elastomeric member. Accordingly, the elastomeric member retracts in the desired direction of shirring as soon as the encapsulating restraint member is ruptured or removed.

Still another example of an elastically shirrable segment of the present invention comprises an elastomeric member which, when stretched, exhibits a discontinuous or irregular surface. The discontinuous surface could be in the form of openings in a lattice or in the form of indentations, voids, recessed areas, raised areas or an otherwise textured surface. A rigidifying member that extended into these openings, indentations, voids or recessed areas or which was penetrated by raised areas on the elastomeric member while the elastomeric member was in an extended condition can be used to restrain the elastomeric member and prevent it from retracting without the need for adhesive bonding of the rigidifying member to the elastomeric member. Removal of the rigidifying member and release of tension in the affected portion of the tensioned elastomeric member can be accomplished by mechanical manipulation of the composite member or by stripping away of the rigidifying member to disengage the rigidifying member from the openings, indentations, voids, recessed areas or raised areas in or on the tensioned elastomeric member.

Because there is little or no adhesive bond between the rigidifying member and the prestretched elastomeric member, the force, particularly the peel force, needed to cause relative movement between the rigidifying member and the stretched elastomeric member is quite low. Conversely, the mechanical interlocking of the prestretched and tensioned elastomeric member and the rigidifying member provide a relatively high resistance to the shear forces imposed by the tension in the prestretched elastomeric member. Tension in the elastomeric member will be released as soon as the appendages or irregularities on the surface of the rigidifying member which extend into their corresponding relief sites in the expanded elastomeric member are withdrawn or as soon as the raised areas on the expanded elastomeric member are withdrawn from their corresponding relief sites in the rigidifying member. It is of course recognized that the rigidifying member and the stretched elastomeric member may each exhibit both types of irregularities, i.e., raised areas and relief sites. In the latter event, securement of the prestretched elastomeric member and the rigidifying member to one another occurs primarily by engagement of complementary raised areas and relief sites with one another.

Regardless of the particular configuration, elastically shirrable segments of the aforementioned type are particularly well suited for consumer activation, since they are highly effective in maintaining the elastomeric member in a prestretched and tensioned condition throughout handling and processing operations, yet they require very little force to activate, i.e., they are very strong in shear, but very weak in peel. The peel force can, of course, be adjusted upwardly if desired by increasing the degree of mechanical engagement or by providing a degree of bonding in addition to mechanical engagement of the irregular surfaces.

Exemplary Embodiments

As pointed out earlier herein, numerous benefits afforded by practicing the present invention can be obtained in a variety of ways. The following exemplary embodiments have been described in the environment of disposable diaper fastening systems constructed for the most part with double-sided adhesive tape merely for ease of illustration. The materials and construction techniques described in the preceding paragraphs can be substituted, as desired, without departing from the spirit and scope of the present invention, as described in the appended claims. Like numerals are utilized throughout the accompanying Drawing Figures and descriptions to represent like elements.

EXAMPLE I

Consumer Activated Elasticized Tape Tab with Pressure Sensitive Adhesive on Uppermost Surface The elasticized fastening system embodiment 120 of the present invention schematically depicted in FIG. 1 comprises a pliable article, such as the waistband of a disposable diaper 80, said waistband having first and second end portions 1 and 2, respectively, which are to be elastically secured to one another. The end portions 1 and 2, which are illustrated in simplified form throughout the accompanying Drawing Figures may be comprised of single or multiple layers of the type normally used to construct a disposable diaper waistband. For a representative disposable diaper waistband construction see, for example, commonly assigned U.S. Pat. No. 3,860,003 issued to Buell on Jan. 14, 1975, which patent is hereby incorporated herein by reference. The only requirement of the end portion 1 is that it be sufficiently pliable that it is capable of shirring when the tension is released in the prestretched and tensioned elastomeric member comprising an element of the present invention.

The first end portion 1 of elasticized fastening system embodiment 120 of the present invention includes a prestretched and tensioned elastomeric member 15 that spontaneously shirrs that portion of the article to which it is secured when the releasable portion 32 of the rigidifying member 28 is separated from the prestretched and tensioned elastomeric member by the person affixing the article in position. This is accomplished in the illustrated embodiment 120 by incorporatig the rigidifying member 28 into an adhesive tape fastening system of the type often used to secure the waistband of a disposable diaper about the waist of an infant.

Figure 1A:
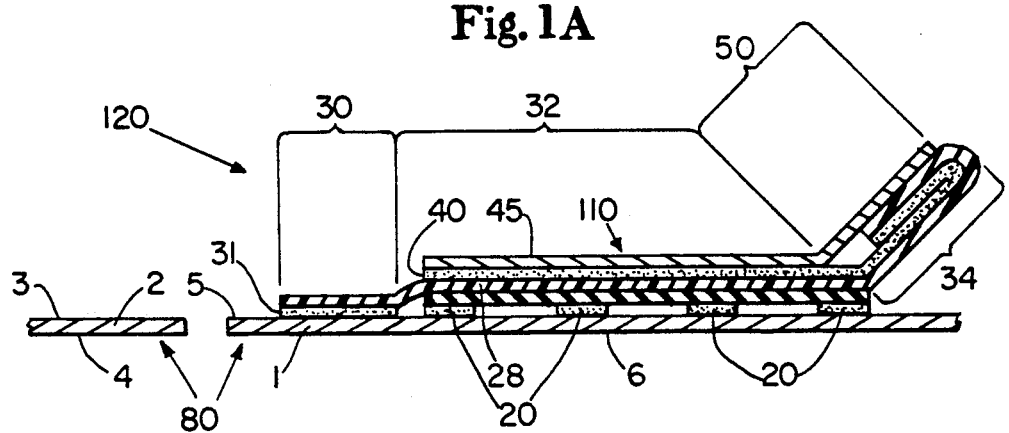
FIG. 1A is a simplified cross-sectional illustration of the article of FIG. 1 taken at a point corresponding to section line 1A—1A in FIG. 1.
Figure 1B:
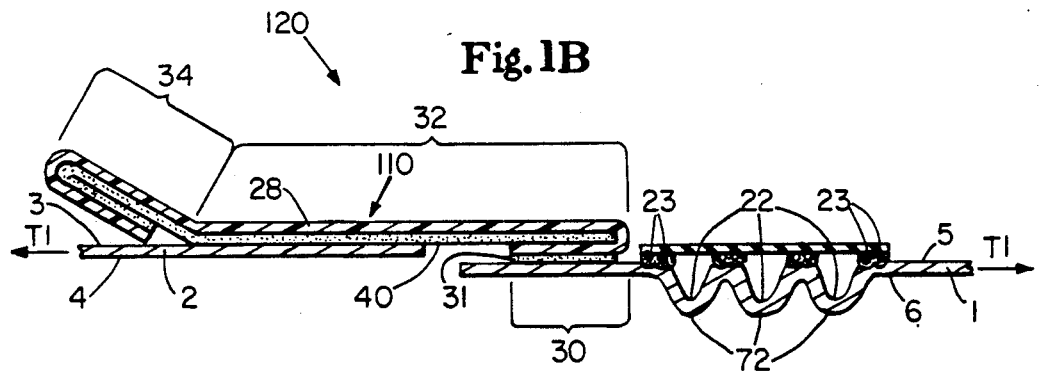
FIG. 1B is a cross-sectional illustration of the first and second end portions of the article shown in FIG. 1 after the releasable portion of the rigidifying member has been separated from the prestretched and tensioned elastomeric member, thereby causing shirring of the first end portion of the article when it is secured to the second end portion of said article while subject to a relatively low level of tenions, $T_1$.
Figure 1C:
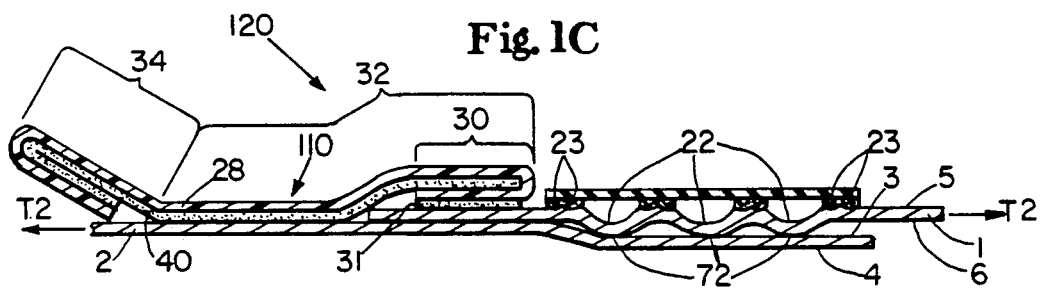
FIG. 1C is an illustration of the end portions of the article shown in FIG. 1 when a higher level of tension, $T_2$, is applied at the time the first end portion of the article is secured in overlapping relation to the second end portion of the article by means of the releasable portion of the rigidifying member.

The exemplary elasticized fastening system embodiment 120 shown in FIGS. 1 through 1C was made up of two opposing end portions 1, 2 of a pliable article 80, such as a disposable diaper waistband, and a composite laminate structure 110. The composite laminate structure 110 was fabricated using the following materials and procedure:

Materials

Prestretched and tensioned elastomeric member (15)—#4141 Soft-Stretch Elastic (natural rubber and polyester thread) having an undeformed thickness and width of about 1/32 inches by about 11/16 inches, respectively, as available from Dritz, Spartanburg, SC.

Rigidifying member (28)—6 mil thick PET-G (glycol modified film—#6763 [poly]ethylene terephthalate) as available from Eastman Chemical Products, Kingsport, TN.

Double-sided adhesive tape (20, 40, 70)—3-M Medical Transfer Adhesive Tape, #1524 as available from 3-M Medical Products Div., St. Paul, Minn.

Adhesive used for bond (31)—Dow 355 Medical Adhesive as available from Dow Corning Corp., Midland, Me. This material was used in the manner of a contact cement and was applied to both surfaces prior to bringing the surfaces in contact with one another.

Release Paper (45)—Adhesive Tape Release Paper as available from 3-M, St. Paul, Minn. The release paper employed on the exemplary embodiments was actually removed from the #1524 3-M tape and reused.

The above web materials were cut to desired lengths and widths needed to construct the samples. Where the starting width of certain of the webs was insufficient, multiple strips of the material were placed side-by-side to make up the desired width.

Equipment

Thermal Impulse Sealer Model 24" LAB-SP (with ¾"×24" heating element) as available from Vertrod Corporation, Brooklyn, NY.

Construction Procedure for the Composite Laminate Structure 110

The Dritz elastomeric member 15 was extended to about twice its original untensioned length and was held expanded as it was placed into the sealing jaws of the Vertrod Impulse Sealer. This prestretched and tensioned elastomeric member 15 was secured in its prestretched and tensioned condition by laminating its uppermost surface to the lowermost surface of a rigidifying member 28 comprising a coextensive strip of Pet-G film using a heat setting of approximately 165° Fahrenheit (74° Centigrade) and a gauge pressure setting of 30 pounds per square inch on the Vertrod Sealer. The heat and pressure produced a degree of mechanical interlocking sufficient to maintain the prestretched elastomeric member in a tensioned condition when the cooled laminated material was removed from the sealing jaws.

End sections of the resultant laminate were separated from one another and the elastomer was trimmed back to create tabs of rigidifying material at opposite ends of the prestretched and tensioned elastomeric member 15. One of the tabs, identified as 30 in FIGS. 1 and 1A, comprises the portion of the rigidifying member which is ultimately secured in fixed relation to the first end portion of the article.

Double-sided adhesive tape 40 was applied to the top side of the releasable portion 32 of the rigidifying member 28 in the area directly over the prestretched and tensioned elastomeric member 15 as well as on one of the tab portions of the rigidifying member extending beyond the elastomeric member. The tab portion including the double sided adhesive tape 40 was thereafter folded over upon itself to create a lift tab 34, as generally shown in FIGS. 1 and 1A.

A layer of release paper 45 was applied over the exposed adhesive on the top side of the layer of double-sided adhesive tape 40 and a gripping tab 50 for removing the release paper was allowed to project over the area of the folded back lift tab 34, thereby forming the composite laminate structure 110 shown gnerally in FIGS. 1 and 1A.

Affixing a Pair of Composite Laminate Structures 110 to the Opposing End Portions of a Waistband of a Disposable Diaper 80

One of the previously described composite laminate structures 110 was applied to each of the identical end portions 1 of the rear wasitband of a disposable baby diaper 80. This involved removing the normal, non-elasticized refastenable tape tabs from an Ultra Pampers Disposable Diaper, as available from The Procter & Gamble Co., Cincinnati, Ohio. Each composite laminate structure 110 was then applied to the outermost or backsheet surface 5 of one of the first end portions 1 of the rear waistband of the diaper about one inch below the top edge of the diaper, near the original tape location. (In Drawing FIGS. 1 through 1E the outermost or backsheet surface of the diaper comprises the uppermost surfaces 5 and 3 of end portions 1 and 2, respectively.)

Dow 355 Medical Adhesive was applied on the lowermost surface of tab 30 and to the opposing surface 5 of end portion 1 to form a bond 31 securing the fixed portion of the rigidifying member 28 to the uppermost surface 5 of the first end portion 1 of the diaper waistband. Four discrete strips 20 of the double-sides adhesive tape were applied at four discrete locations to the lowermost surface 16 of the prestretched and tensioned elastomeric member 15 to secure the prestretched and tensioned elastomeric member to the uppermost surface 5 of the first end portion 1 of the article 80, as generally shown in FIG. 1A.

The resultant disposable diaper having a pair of composite laminate structures 110 affixed to the opposite end portions 1 of its rear waistband was applied to a baby model using a procedure generally similar to that used to apply disposable diapers which do not employ an elasticized element in their fastening systems. First the release paper 45 was removed from the top of the composite structure 110 using the tab 50 to expose the uppermost surface of the double-sided adhesive tape 40. Then the releasable portion 32 of the rigidifying member 28 was lifted from its original position using the folder over lift tab 34 and the exposed surface of the double sided adhesive tape 40 was used to secure the releasable portion 32 of the rigidifying member 28 to the uppermost or backsheet surface 3 of the second end portion 2 of the diaper waistband, as generally shown in FIG. 1B. The act of lifting the releasable portion 32 of the composite structure 110 allowed the prestretched and tensioned elastomeric member 15 to recover to near its original length prior to stretching, causing the first end portion 1 of the diaper to shirr in that area, as generally shown in FIG. 1B.

FIG. 1B illustrates the condition which results when the first end portion 1 and the second end portion 2 of the article 80 are subject to a relatively low degree of tension, $T_1$, when the exposed surface of the double-sided adhesive tape 40 on the releasable portion 32 of rigidifying member 28 is attached to the uppermost surface 3 of the second end portion 2 of the article. When the opposed end portions 1, 2 are subject to a relatively low degree of tension, $T_1$, most of the tension in the prestretched elastomeric member 15 is released. Release of most of the tension in the prestretched elastomeric member 15 causes a substantial degree of shirring of the first end portion of the article in the areas intermediate the discrete double-sided adhesive tape bonds 20 securing the elastomeric member to the uppermost surface 5 of the first end portion 1 of the article. This produces relatively large gathers generally indicated at 22 which are normally transmitted, at least to a degree, all the way through the article to also form gathers 72 on the lowermost surface 6 of the first end portion of the article. In addition, release of most of the tension in the prestretched elastomeric member 15 permits a much finer scale gathering of the article in those areas where the discrete segments of double-sided adhesive tape 20 secure the elastomeric member 15 to the end portion 1 of the article. These finer scale gathers are generally indicated at 23.

Figure 1D:
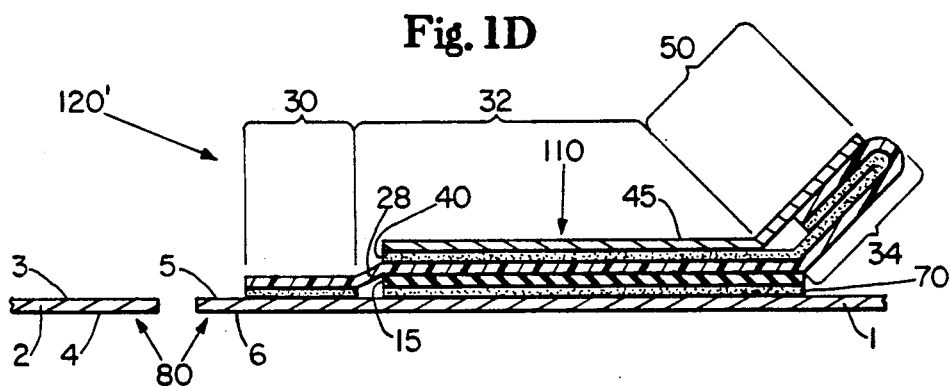
FIG. 1D is a cross-sectional view of an alternative embodiment of an article of the present invention which differs from the embodiment of FIG. 1 primarily with respect the manner in which the prestretched and tensioned elastomeric member of the composite structure is secured to the uppermost surface of the first end portion of the article.
Figure 1E:
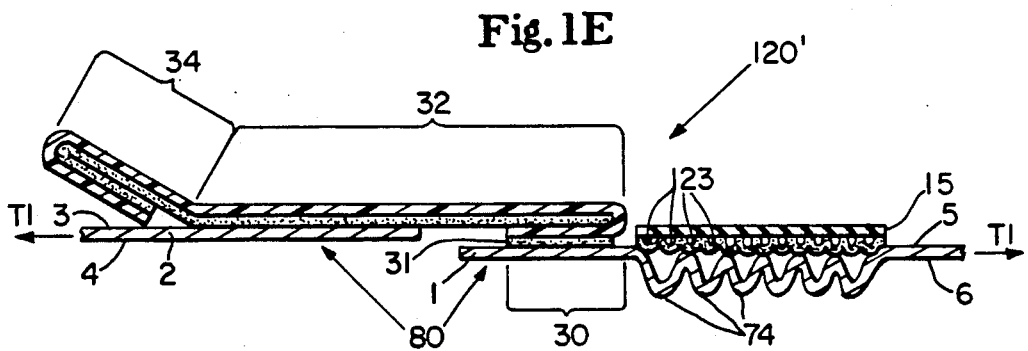
FIG. 1E is a cross-sectional view of the article shown in FIG. 1C after the releasable portion of the rigidifying member has been separated from the prestretched and tensioned elastomeric member and secured to the uppermost surface of the second end portion of the article while it is subject to a relatively low level of tension, $T_1$.

Accordingly, it will be appreciated that the discrete segments of double-sided adhesive tape 20 shown in fastening system embodiment 120 of FIGS. 1 through 1C could, if desired, be replaced by a single, continuous strip of double-sided adhesive tape 70 (or for that matter any other suitable continuous securement means), as generally shown in fastening system embodiment 120' of FIG. 1D. While the overall degree of contraction of elastomeric member 15 will be about the same when the opposing end portions 1, 2 of embodiment 120' are subjected to the same level of tension, $T_1$ (compare FIG. 1E with FIG. 1B), the size and frequency of the gathers 123 formed in the uppermost surface of end portion 1 of embodiment 120' will be much finer than the size and frequency of the gathers 22 in embodiment 120. In most instances, the size and frequency of gathers 123 in embodiment 120' will closely approximate the size and frequency of the gathers 23 in embodiment 120 shown in FIG. 1B. However, as can be seen from FIG. 1E, the size and frequency of the gathers 74 formed in the lowermost surface 6 of the article does not necessarily correspond to the size and frequency of the gathers 123 formed in the uppermost surface of the article.

The size and frequency of the gathers formed in the surface of an article which is opposite the surface to which the elastomeric member is secured will depend upon such factors as the number of layers of material comprising the article, the degree of bonding therebetween, the stiffness of the various layers and the like. If, for example, the first end portion of the article comprises a single layer of very pliable material, the size and frequency of gathers on the lowermost surface of the article will be approximately the same as that of the gathers on its uppermost surface, i.e., the surface to which the elastomeric member is secured. Conversely, if the first end portion of the article comprises multiple layers of material which tend to delaminate from one another, the size of the gathers on the lowermost surface will generally be larger and their frequency lower than for the gathers on uppermost surface.

From the foregoing, it will be appreciated that the size and frequency of the gathers to be induced in the uppermost and owermost surfaces of the article to be elastically secured can be adjusted in any desired direction by selection of the appropriate securement means between the prestretched and tensioned elastomeric member and the first end portion of the article.

Returning again to fastening system embodiment 120, the first and second end portions of the article are secured to one another in a butt joint configuration in FIG. 1B. FIG. 1C discloses the situation which would exist if the first and second end portions 1 and 2, respectively, of article 80 are secured in overlapping relation to one another while subject to a much higher degree of tension, $T_2$.

Although a single fastener system embodiment 120 of the type shown in FIGS. 1 and 1A is sufficient to impart elasticity when securing an article about an object of predetermined cross-section, in the case of a disposable diaper it is recognized that two such connections will normally be made on opposing sides of the waistband, and that tension cannot be imparted to the waistband until after the first such connection has been made. The condition shown in FIG. 1C is most typical of what would be experienced in affixing the second such fastener system to elastically encircle the waist of an infant with a disposable diaper. As will be appreciated by those skilled in the art, subjecting the first and second end portions of the article to a higher degree of tension, $T_2$, restores a greater degree of tension to the elastomeric member 15. Elongation of the elastomeric member 15 results in a decrease in the vertical amplitude of both the large gathers 22, 72 and the small gathers 23 in the first end portion 1 of the article 80. A similar appearance will likewise be exhibited by the first such fastener system to be affixed during the diaper application process, sicne the tension, $T_2$, is substantially uniformly distributed about the entire diaper waistband as soon as the second such fastener system is secured in place.

EXAMPLE II

Consumer Activated Elasticized Tape Tab With Pressure Sensitive Adhesive on Lowermost Surface The elasticized fastening system embodiment 220 shown in the simplified perspective view of FIG. 2 is somewhat similar to embodiment 120 of Example I. The composite laminate structure 210 comprises a pair of prestretched and tensioned elastomeric members 215 secured in fixed relation to a rigidifying member 228 having a releasable portion 232 and a fixed portion 230.

However, there are several differences between the Example I embodiment 120 of FIG. 1 and the Example II embodiment 220 of FIG. 2. The pressure sensitive adhesive used to secure the releasable portion 232 of the composite laminate structure 210 to the second end portion 2 of the diaper 80 is located on the lowermost rather than the uppermost surface of rigidifying member 228. In addition, it comprises multiple strips of double-sided adhesive tape 278 flanking a pair of prestretched and tensioned elastomeric member 215. A pair of double-sided adhesive tape strips 275 coinciding with prestretched and tensioned elastomeric members 215 are used to secure the prestretched and tensioned elastomeric members 215 to a layer of polymeric film 235 which in turn is secured to the first end portion 1 of the article.

Since the adhesive used to secure the first and second end portions of the article to one another is protected by means of its downward orientation in embodiment 220, the release paper (element 45 in FIG. 1) was omitted.

Finally, and perhaps most importantly, the composite laminate structure 210 used in fastening system embodiment 220 was designed to attach to the topsheet side 6 (shown as the uppermost surface in FIG. 2) of the diaper rather than the backsheet side 5 (shown as the lowermost surface in FIG. 2). This allows securement of the releasable portion 232 of the rigidifying member to the backsheet (lowermost) surface 3 of end portion 2 of the diaper waistband, as would normally be desirable in applying a disposable diaper to an infant.

Material Change.

The elastomeric member 15 used in elasticized fastening system embodiment 120 of FIG. 1 was comprised of #4141 Soft-Stretch Elastic. This material was replaced with an alternative elastomeric member 215 comprised of #5842 Soft-Stretch Elastic also available from Dritz, Spartanburg, S.C.

Construction Procedure for the Composite Laminate Structure 210

The same general construction procedure that was used in constructing Example I composite laminate structure embodiments 110 was also used in constructing Example II composite laminate structure embodiments 210, with the following changes:

The pair of Dritz elastomeric members 215 was secured to the lowermost surface of the releasable portion 232 of rigidifying member 228 while prestretched and tensioned using the Vertrod sealer at a heat setting of approximately 175° Fahrenheit (74° Centrigrade) and a gauge pressure setting of 30 pounds per square inch. End tabs 230 and 234 were prepared generally in accordance with the procedure used in Example I. However, end tab 234 was folded oppositely from end tab 34, as generally shown in FIG. 2.

Referring to FIG. 2, parallel cross-sections along section lines 2A—2A and 2B—2B have been taken to more clearly illustrate that the interior of the composite laminate structure 210 is not uniform across the entire depth of the rigidifying member 228. Three strips of double-sided adhesive tape 278 (comprised of the same material as element 20 in embodiment 110 of FIG. 1) were affixed to the lowermost surface of rigidifying member 228, parallel and adjacent to the previously bonded prestretched and tensioned elastomeric members 215. Double-sided adhesive tape strips 275 were also applied to the lowermost surfaces of the prestretched and tensioned elastomeric members 215. FIG. 2A, taken along section line 2A—2A, and FIG. 2B, taken along section line 2B—2B, show the two different instantaneous cross-sections which exist within the composite laminate structure 210 of Example II, as viewed at different points along its depth.

Affixing a Pair of Composite Laminate Structures 210 to the Waistband of a Disposable Diaper 80

Prior to attaching the previously described composite laminate structures 210 to the opposing end portions 1 of the rear waistband of the diaper 80, a layer of polyethylene film 235 (same material as the diaper backsheet) was affixed to the diaper topsheet (located on uppermost surface 6 of end portion 1) using a continuous length of double-sided adhesive tape 236. Dow 355 Medical Adhesive was used to create bond 231 securing the lowermost surface of fixed portion 230 of rigidifying member 228 to one edge of the polyethylene layer 235 and the remaining portion of the composite laminate structure 210 was attached to the polyethylene layer 235 by the double-sided adhesive tape strips 275 secured to the lowermost surface of the prestretched and tensioned elastomeric members 215 (as shown in the instantaneous cross-section of FIG. 2A).

Figure 2B:
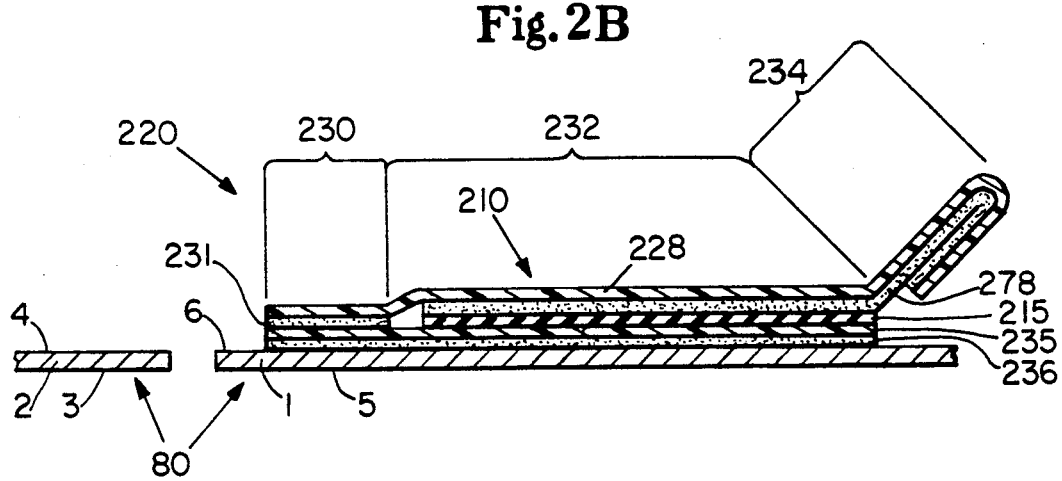
FIG. 2B is an instantaneous cross-sectional view of the article of FIG. 2 taken along section line 2B—2B of FIG. 2.

In the instantaneous cross-section of FIG. 2B it appears that the lowermost surface of double-sided adhesive tape strips 278 do not contact polyethylene film layer 235. This appearance is due to the exaggerated thicknesses used to illustrate the various layers. In actual practice the lowermost surfaces of the double-sided adhesive tape strips 278 also normally contact layer of polyethylene film 235 until the releasable portion 232 of rigidifying member 228 is intentionally separated from the prestretched and tensioned elastomeric members 215 to affix the end portions of the article to one another.

The resultant disposable diaper having a pair of composite laminate structures 210 affixed to its opposing first end portions 1 of its rear waistband was applied to a baby model in a manner somewhat similar to that of Example I. However, since the release paper (45) of Example I was not used in Example II, there was no need to remove it prior to application. The releasable portion 232 of rigidifying member 228 was lifted from its original position using the folded over lift tab 234 and was secured to the backsheet (lowermost) side 3 of end portion 2 of disposable diaper 80 using the exposed adhesive surface of double-sided tape strips 278. (To avoid confusion in interpreting FIGS. 2C and 2D it should be noted that although an adhesive strip 278 is visible in the cross-section of FIGS. 2C and 2D, this is an edge view of the adhesive strip 278 rather than a section through it, since the cross-sections of FIGS. 2C and 2D are taken at a point corresponding to Section Line 2A—2A rather than Section Line 2B—2B.)

Separating the releasable portion 232 of rigidifying member 228 from each of the prestretched and tensioned elastomeric members 215 allows the elastomeric members to recover to near their original length, which creates shirring in the form of relatively small gathers 223 in the topsheet (uppermost) surface 6 of end portion 1 of disposable diaper 80. This translates into somewhat larger gathers 274 on the backsheet (lowermost) surface 5 of end portion 1 of the diaper.

Figure 2C:
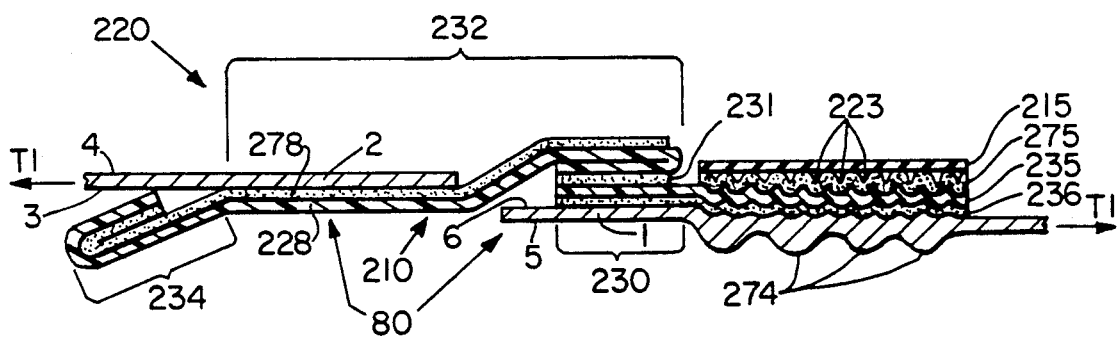
FIG. 2C is a cross-sectional illustration of the end portions of the article shown in FIG. 2 taken at a point corresponding to section line 2A—2A of FIG. 2 after the releasable portion of the rigidifying member has been separated from the prestretched and tensioned elastomeric member and secured to the lowermost surface of the second end portion of the article while it is subject to a relatively low level of tension, $T_1$.
Figure 2D:
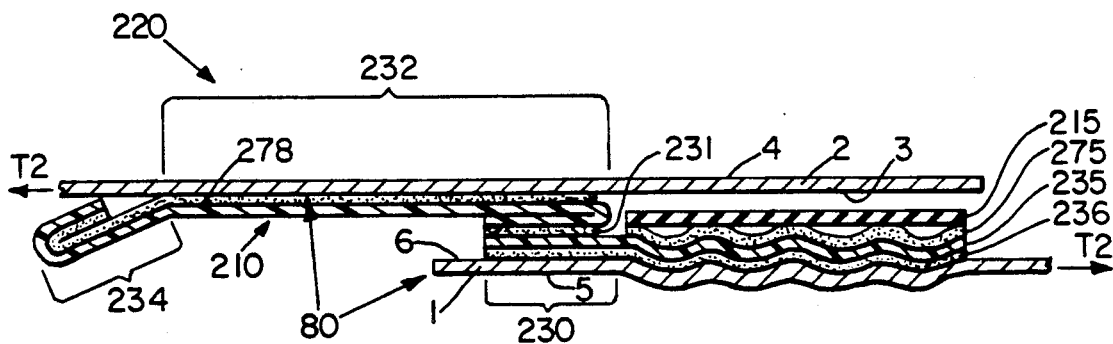
FIG. 2D is a cross-sectional illustration of the end portions of the article shown in FIG. 2 taken at a point corresponding to section line 2A—2A of FIG. 2 when the releasable portion of the rigidifying member is secured to the lowermost surface of the second end portion of the article while subject to a greater degree of tension, $T_2$.

FIG. 2C illustrates the condition which exists when the first end portion 1 is secured to the second end portion 2 in butt joint fashion while subject to a relatively low degree of tension, $T_1$. FIG. 2D depicts the condition which exists when a greater degree of tension, $T_2$, is applied to the diaper waistband during an overlapping attachment process. Due to the increased tension, $T_2$, gathers at locations 223 and 274 are seen to be less in amplitude than for tension, $T_1$, shown in FIG. 2C.

Example II Variation

Figure 2E:
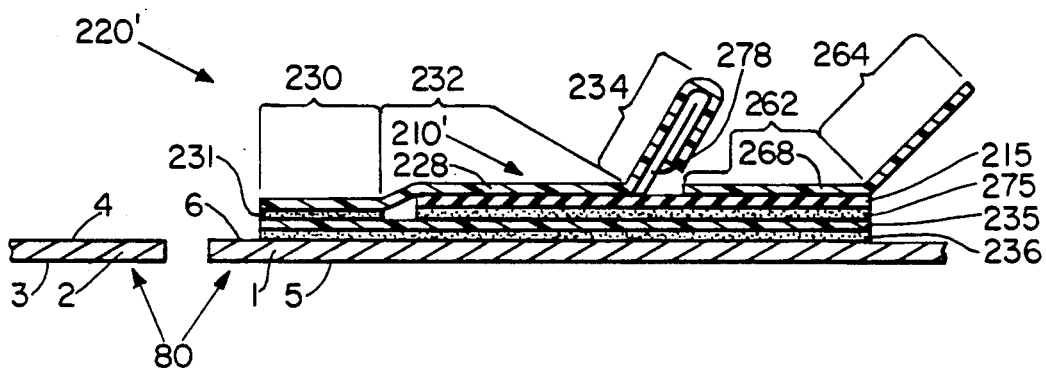
FIG. 2E is a simplified cross-sectional view of the first and second end portions of another article of the present invention, said article being somewhat similar to that shown in FIG. 2, but including a secondary rigidifying member which can be removed from the composite laminate structure independently of the primary rigidifying member.

The cross-section of FIG. 2E, which is comparable in most respects to the cross-section of FIG. 2A, shows an alternative embodiment 220' of an elasticized fastening system of the present invention. Embodiment 220' is a variation of Example II in which an additional feature is added to the basic concept of embodiment 220. Elasticized fastening system embodiment 220' of FIG. 2E permits sequenced release of tension in the prestretched and tensioned elastomeric members at different points in time. The same basic materials and general construction procedures were used to make fastening system embodiment 220' shown in FIG. 2E as were used to make fastening system embodiment 220 of FIG. 2. However a secondary rigidifying member 268 was added and elastomeric members 215 and their associated attachment systems were longitudinally extended.

Secondary rigidifying member 268 is preferably comprised of a restraint portion 262 and a lift tab 264. If desired, it can be comprised of an additional section of the same Pet-G film used to form rigidifying member 228. It is preferably bonded to the extended portions of elastomeric members 215 using the same technique that was used to bond the primary rigidifying member 228 to prestretched and tensioned elastomeric members 215, i.e., the application of heat and pressure.

An advantage of fastening system embodiment 220' shown in FIG. 2E relative to embodiment 220 shown in FIG. 2 is that the additional section of prestretched and tensioned elastomer can be activated independently of the remaining portions of the prestretched and tensioned elastomeric members 215. Removal of secondary rigidifying member 268 can be performed at the time the article is applied to the wearer by the end user, or by the manufacturer of the article at any time subsequent to affixing the composite laminate structure 210' to the article to be elastically secured.

Figure 2F:
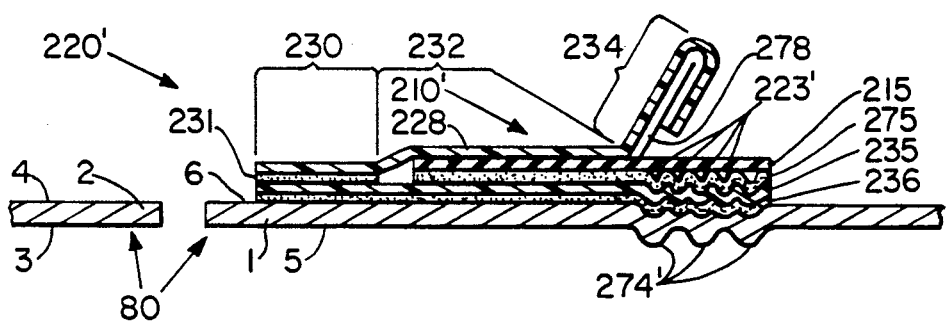
FIG. 2F is a cross-sectional illustration generally similar to that of FIG. 2E, but showing the condition which exists after the secondary rigidifying member has been separated from the remainder of the composite laminate structure.
Figure 2G:
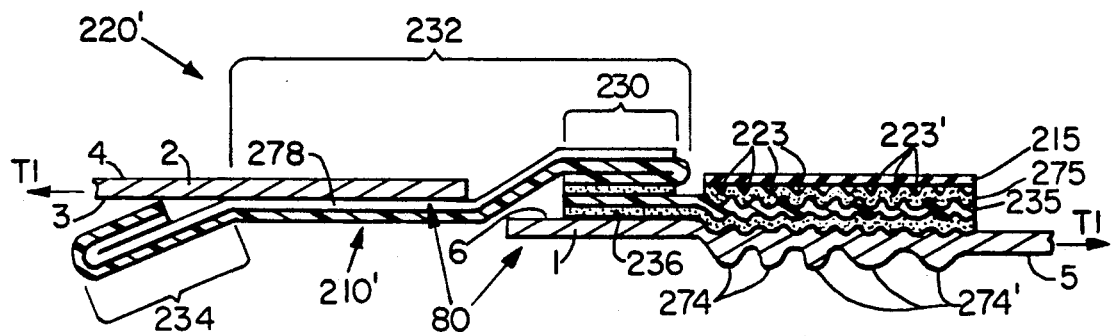
FIG. 2G is a cross-sectional illustration of the article of FIG. 2E after the primary rigidifying member has been separated from the prestretched and tensioned elastomeric member and secured to the lowermost surface of the second end portion of the article while it is subject to a relatively low level of tension, $T_1$.

FIG. 2F illustrates the condition of fastening system embodiment 220' after the secondary rigidifying member 268 has been removed to produce article shirring in the form of gathers at 223' and 274'. FIG. 2G depicts the condition which exists after embodiment 220' has been fully activated by securing end portions 1 and 2 of the waistband of disposable diaper 80 to one another in a butt joint fashion while subject to a relatively low degree of tension, $T_1$. The total amount of the diaper which is subject to shirring can easily be controlled by selecting the appropriate overall length for elastomeric members 215 and their associated rigidifying members and attachment systems.

The amount of shirring to be provided by the manufacturer and the amount of shirring to be provided by the consumer can likewise be adjusted, as desired, by appropriately balancing the lengths of primary rigidifying member 228 (removed by the consumer) and secondary rigidifying member 268 (removed by the manufacturer) relative to one another. The amplitude of the gathers in the shirred portion or portions of the installed article will, of course, depend upon the level of tension applied at the time the first and second end portions of the article are secured to one another.

In still another embodiment of the present invention (not shown), the function served by secondary rigidifying member 268 could be supplied by one or more components comprising a permanent portion of the manufacturing system used for producing the composite laminate structure 210' or for affixing it to the article to be elastically secured. For example, the function of secondary rigidifying member 268 could be filled by a moving conveyor belt which travels with the composite laminate structure 210' during the affixing process and which separates from the moving web of articles after the affixing process has been completed. This would permit the manufacturer to provide an elastically shirred article to the end user, while avoiding the handling problems normally associated with stripping away and discarding a portion of the composite laminate structure at high speed.

EXAMPLE III

Figure 3:
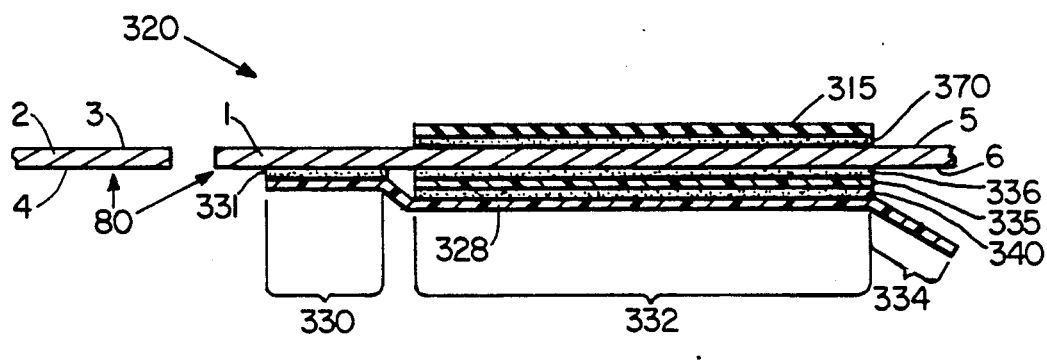
FIG. 3 is a cross-sectional illustration of the first and second end portions of another article of the present invention, said article being somewhat similar to those shown in FIGS. 1 and 2, but wherein a prestretched and tensioned elastomeric member is secured to the uppermost surface of the first end portion of the article and a rigidifying member is secured to the lowermost surface of the first end portion of the article such that the prestretched and tensioned elastomeric member is prevented from contracting so long as the releasable portion of the rigidifying member remains secured to the lowermost surface of the first end portion of the article.

Consumer Activated Elasticized Tape Tab having No Direct Contact between the Prestretched and Tensioned Elastomeric Member and the Rigidifying Member The hypothetical elasticized fastening system embodiment 320 illustrated in cross-section in FIG. 3 differs from the exemplary embodiments described earlier herein in that it is constructed directly on the article to be elasticized rather than as a composite laminate structure. It also differs from the embodiments described earlier herein in that there is no direct contact between the prestretched and tensioned elastomeric member 315 and the rigidifying member 328. Rather, the prestretched and tensioned elastomeric member 315 is secured to the backsheet (uppermost) side 5 of the first end portion 1 of the disposable diaper 80 and the rigidifying member 328 is secured to the topsheet (lowermost) side 6 of the first end portion of the diaper. The restraint forces imposed by the rigidifying member on the prestretched and tensioned elastomeric member are transmitted through the article to be elasticized.

The hypothetical fastening system embodiment 320 illustrated in FIG. 3 may be constructed utilizing the same types of materials described in connection with the earlier exemplary embodiments. For example, a layer of polyethylene film 335 may be secured to the topsheet (lowermost) side 6 of the first end portion of the diaper by means of a section of double-sided adhesive tape 336. Another section of double-sided adhesive tape 340 may be applied to the releasable portion 332 of rigidifying member 328, as generally shown in FIG. 3. The fixed portion 330 of the rigidifying member 328 is also preferably secured to the topsheet (lowermost) side 6 of the first end portion of the diaper either by means of another section of double-sided adhesive tape or by means of the Dow 355 Medical Adhesive to form a bond 331. The opposite end of the rigidifying member 328 is allowed to project beyond adhesive layer 340 to provide a lift tab 334.

The prestretched and tensioned elastomeric member 315 may be adhered to the backsheet (uppermost) side 5 of the first end portion 1 of the disposable diaper 80 by means of another section of double-sided adhesive tape 370. The elastomeric member 315 is, of course, held in a prestretched and tensioned condition during the application process. The tension is maintained in the prestretched elastomeric member 315 by the releasable portion 332 of the rigidifying member 328 until such time as it is separated from the polyethylene layer 335 by means of lift tab 334.

Figure 3A:
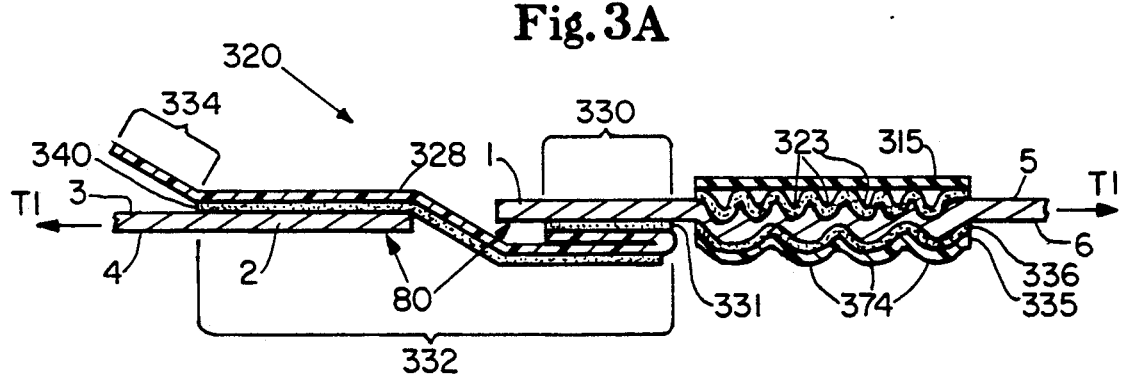
FIG. 3A is an illustration of the end portions of the article shown in FIG. 3 after the releasable portion of the rigidifying member has been separated from the lowermost surface of the first end portion of the article, said releasable portion of the rigidifying member being thereafter secured to the uppermost surface of the second end portion of the article while subject to a relatively low level of tension, $T_1$.

FIG. 3A illustrates the condition which would exist if the releasable portion 332 of the rigidifying member 328 is secured to the backsheet (uppermost) side 3 of the second end portion 2 of disposable diaper 80 while subject to a relatively low degree of tension, $T_1$. Gathers 323, 374 are formed in the first end portion of the article when the releasable portion 332 of the rigidifying member 328 is no longer secured in fixed relation to the prestretched and tensioned elastomeric member 315.

Figure 3B:
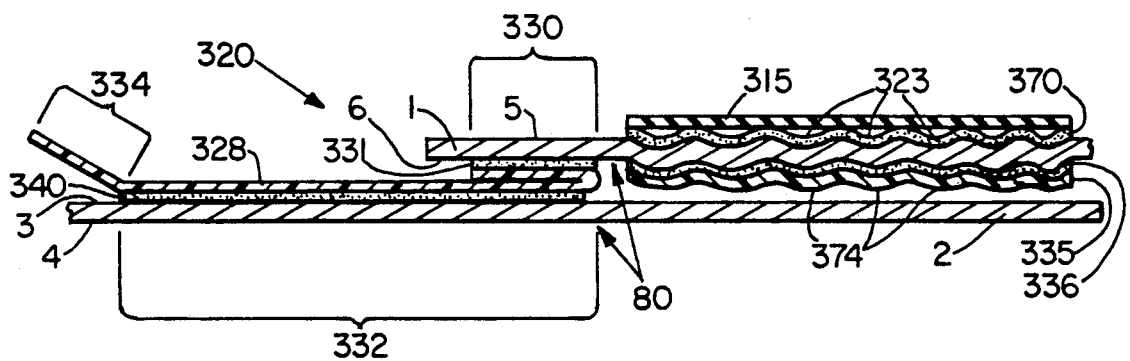
FIG. 3B is an illustration of the end portions of the article shown in FIG. 3 illustrating the condition which exists when the releasable portion of the rigidifying member is subjected to a higher level of tension, $T_2$, while the first end portion of the article is secured in overlapping relation to the uppermost surface of the second end portion of the article.

FIG. 3B illustrates the condition which would exist if the opposing end portions of the article are subjected to a greater degree of tension, $T_2$, at the time the end portions of the article are secured in overlapping relation to one another. Note that the amplitude of gathers 323, 374 decreases as the level of tension increases.

EXAMPLE IV

Figure 4:
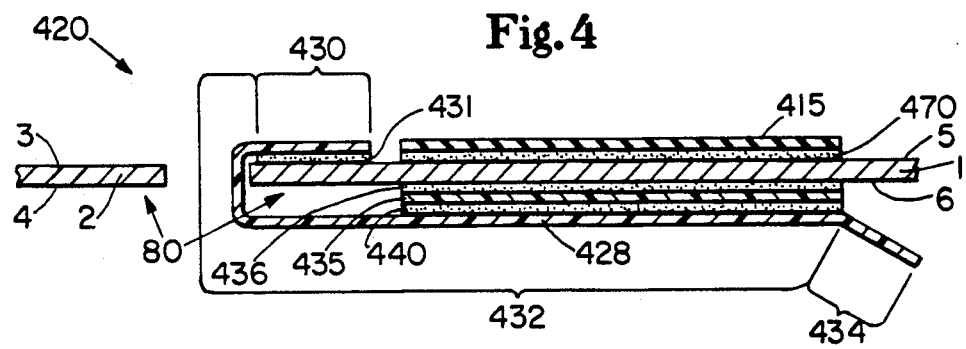
FIG. 4 is a cross-sectional illustration of the first and second end portions of another article of the present invention, said article being somewhat similar to those shown in FIGS 1-3, but wherein the prestretched and tensioned elastomeric member is secured to the uppermost surface of the first end portion of the article and the rigidifying member is secured to both the uppermost and the lowermost surfaces of the first end portion of the article.

Consumer Activated Elasticized Tape Tab With No Direct Bond Between the Prestretched and Tensioned Elastomeric Member and the Rigidifying Member The elasticized fastening system embodiment 420 schematically depicted in the cross-section of FIG. 4 is another example in which the prestretched and tensioned elastomeric member 415 is not in direct contact with the rigidifying member 428. Rather, the prestretched and tensioned elastomeric member 415 is secured to the backsheet (uppermost) surface 5 of the first end portion 1 of the disposable diaper waistband 80. The releasable portion 432 of the rigidifying member 428 is secured indirectly via a layer of polyethylene film 435 to the topsheet (lowermost) surface 6 of the first end portion 1 of the disposable diaper waistband. Unlike fastening system embodiment 320 shown in FIG. 3, the fixed portion 430 of rigidifying member 428 is secured to the backsheet (uppermost) side 5 of the first end portion of the diaper. So long as the releasable portion 432 of the rigidifying member 428 remains in the position shown in FIG. 4, the elastomeric member 415 will be maintained in a prestretched and tensioned condition, i.e., the stiffening effect of the rigidifying member is transmitted through the thickness of the end portion 1 of the diaper waistband 80.

Materials

With the exception of rigidifying member 428, the same basic materials that were used to construct most of the earlier exemplary elasticized fastening system embodiments were used to construct elasticized fastening system embodiment 420.

Rigidifying member (428)—10 mil thick Pet-G (glycol modified film—#6763 [poly]ethylene terephthalate) as available from Eastman Chemical Products, Kingsport, Tenn.

Construction Procedure for Elasticized Fastening System Embodiment 420

The construction procedure for elasticized fastening system embodiment 420 of Example IV was different from the embodiments of Examples I and II. In particular, this execution was constructed directly on the disposable diaper rather than being applied to the diaper as a prefabricated composite laminate structure.

The first step in constructing the elasticized fastening system embodiment 420 involved applying a small section of polyethylene film 435 to the first end portion 1 of the diaper on the topsheet (lowermost) side 6 using a section of double-sided adhesive tape 436. Another section of double-sided adhesive tape 440 was applied to a portion of rigidifying member 428 extending all the way to its free end. The free end of the rigidifying member was thereafter folded upon itself to form lift tab 434. The opposite end portion of rigidifying member 428 was attached to the diaper backsheet (uppermost) side 5 using another section of double-sided adhesive tape 431. The latter portion of the rigidifying member comprised its fixed portion 430.

Releasable portion 432 of rigidifying member 428 was then folded about the edge of the first end portion 1 of the disposable diaper waistband 80 so that the exposed surface of adhesive layer 440 contacted the previously laid polyethylene layer 435 on the topsheet (lowermost) side 6 of the first end portion of the diaper.

Finally, a section of double-sided adhesive tape 470 was applied to the diaper backsheet (uppermost) side 5 in an area coinciding with the releasable portion 432 of rigidifying member 428. A section of Fulflex #9411 rubber comprising elastomeric member 415 was extended to about twice its normal length and held in tension while it was placed in contact with the exposed adhesive surface of the previously laid adhesive layer 470. The resultant elasticized fastening system embodiment 420 is shown in FIG. 4. (It should be noted that this exemplary embodiment did exhibit some tendency to curl the first end portion of the diaper waistband. However, this tendency could be reduced by using a thicker or a stiffer rigidifying member 428 and/or by improving the bonds between the various layers comprising the diaper laminate. Alternatively an elastomeric member having a lower modulus of elasticity could be employed.)

A disposable diaper 80 having an elasticized fastening system embodiment 420 at each end portion of its rear waistband was applied to a baby model in a manner somewhat similar to that of Example II.

Figure 4A:
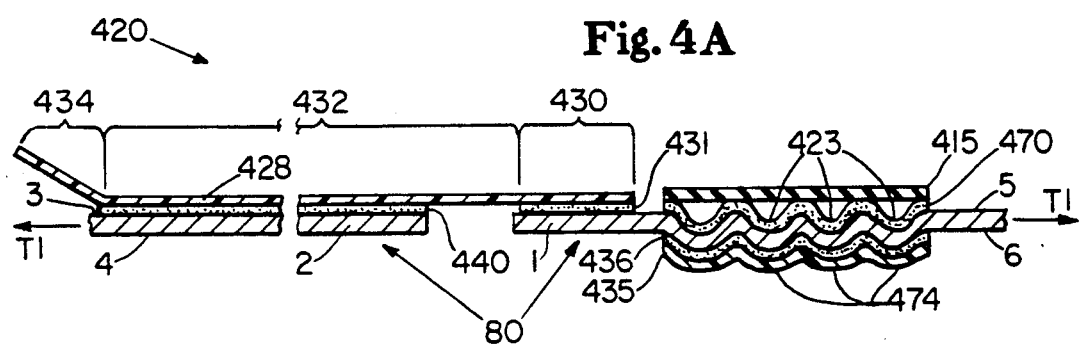
FIG. 4A is a cross-sectional illustration of the first and second end portions of the article shown in FIG. 4 after the releasable portion of the rigidifying member has been separated from the lowermost surface of the first end portion of the article and secured to the uppermost surface of the second end portion of the article while subject to a relatively low degree of tension, $T_1$.

The releasable portion 432 of rigidifying member 428 was lifted from its original position using lift tab 434 and secured to the backsheet (uppermost) side 3 of end portion 2 of the disposable diaper 80 using the exposed adhesive surface of layer 440, as generally illustrated in FIG. 4A. FIG. 4A shows the degree of shirring which occurs in the form of gathers 423, 474 when the diaper waistband is subjected to a relatively low degree of tension, $T_1$, at the time the first and second end portions are secured to one another.

Figure 4B:
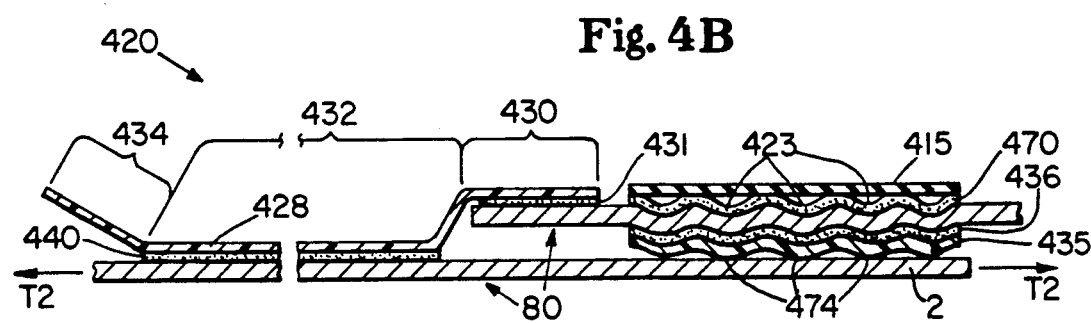
FIG. 4B is an illustration of the condition which exists when a higher level of tension, $T_2$, is applied when the first end portion of the article is secured in overlapping relation to the second end portion of the article by means of the releasable portion of the rigidifying member.

FIG. 4B illustrates the condition which exists when a greater degree of tension, $T_2$, is applied to the waistband at the time of securement. Note that the amplitude of the gathers 423, 474 decreases as the level of tension increases.

EXAMPLE V

Figure 5:
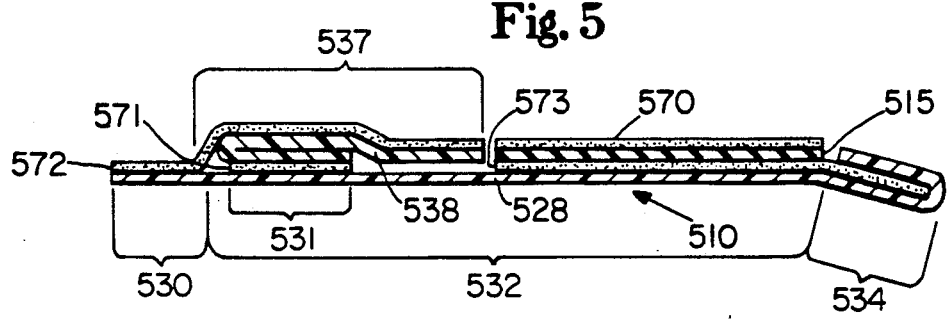
FIG. 5 is a cross-sectional illustration of a composite laminate structure of the present invention prior to its application to a first end portion of an article to be elastically secured to a second end portion of the article.
Figure 5A:
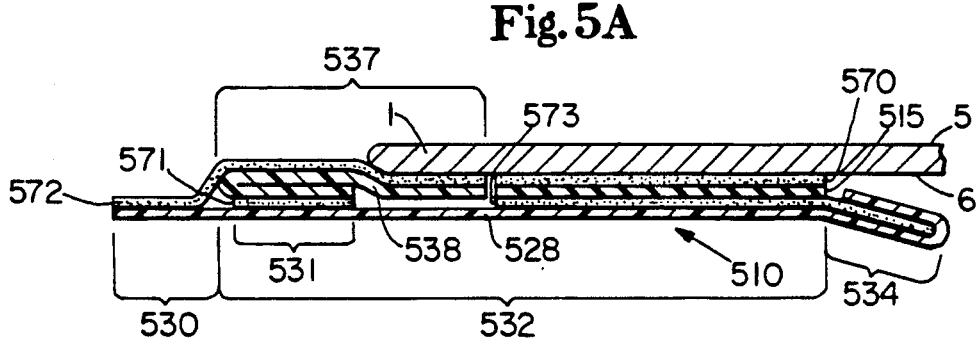
FIG. 5A is a cross-sectional illustration of the composite laminate structure shown in FIG. 5 after it has been applied to the lowermost surface of the first end portion of the article.
Figure 5B:
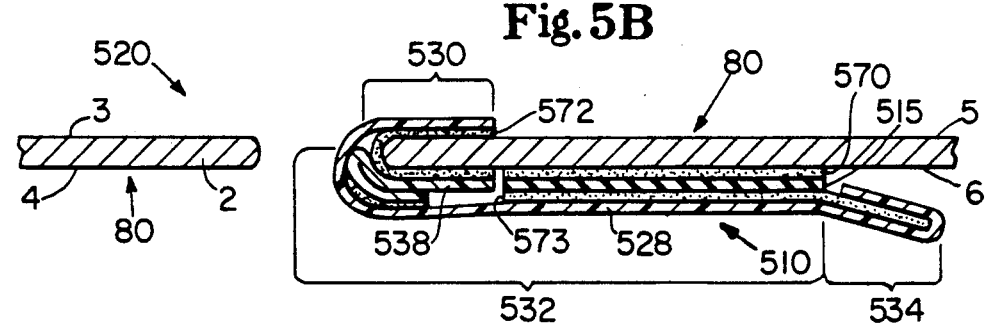
FIG. 5B is a cross-sectional illustration of the composite laminate structure shown in FIGS, 5 and 5A after it has been completely affixed to the first end portion of the article.

Consumer Activated Elasticized Tape Tab which can be Formed from Continuous Webs The elasticized fastening system embodiment 520 shown in simplified form in the cross-section of FIG. 5B is somewhat similar to embodiment 220 of Example II. Embodiment 520 includes a composite laminate structure 510 which is particularly well suited to being manufactured from continuous webs of material by a continuous machine direction assembly process. The continuous composite web thus formed may either be fed into rolls for storage or cut into discrete segments and applied directly to moving webs comprised of interconnected diapers on existing diaper converting lines with little or no modification to existing tape tab applicating systems. This permits the continuous, high-speed manufacture of articles exhibiting elasticization in a direction substantially perpendicular to the direction of web travel, i.e., in the cross-machine direction.

The composite laminate structure 510 generally illustrated in FIG. 5 comprises a single prestretched and tensioned elastomeric member 515 secured in a fixed relation to a rigidifying member 528 having a releasable portion 532 and a fixed portion 530.

Material Change

Elastomeric member 515—Fulflex #9411 Natural Rubber 1" wide×0.007" thick (1N2732as available from Fulflex, Inc., Middletown, R.I.

Construction Procedure for the Composite Laminate Structure 510

The construction procedure used for the Example V composite laminate structure embodiments 510 did not use the Vertrod heat sealer to bond the elastomeric member 515 to the rigidifying member 528. Instead, the entire assembly process for this example was accomplished using double-sided adhesive tape.

Referring to FIG. 5, composite laminate structure 510 was assembled by first applying double-sided adhesive tape 573 to the right hand portion of the Pet-G rigidifying member 528. The Pet-G material 528 was then folded upon itself to create lift tab 534 at the free end of the releasable portion 532 of rigidifying member 528.

The elastomeric member 515 was stretched and held in tension as a section of double-sided adhesive tape 570 was placed on its uppermost surface. While still being held in tension, elastomeric member 515 and the double-side adhesive tape 570 were attached to the exposed adhesive tape strip 573 previously secured to rigidifying member 528, as generally shown in FIG. 5.

A shorter section of Pet-G material 538 was then attached to rigidifying member 528 in area 531 using a segment of double-sided adhesive tape 571. This section of material acts as a secondary securement member. The unadhered portion 537 of the Pet-G layer 538 was folded back upon itself, as generally illustrated in FIG. 5. Another segment of double-sided adhesive tape 572 was finally applied to the entire uppermost folded back portion 537 of layer 538 as well as to the uppermost exposed portion 530 of rigidifying member 528. The resultant composite laminate structure 510 is illustrated in FIG. 5.

Although the same type of double-sided adhesive tape was used for elements 570 and 573 in constructing the composite laminate structure embodiments 510 of Example V, this was done to simplify the assembly procedure. In a particularly preferred embodiment of the present invention the relative adhesive properties at these locations would differ from one another. In particular, the adhesion at the interface between adhesive layer 570 and prestretched and tensioned elastomeric member 515 should be stronger than the adhesion at the interface between prestretched and tensioned elastomeric member 515 and adhesive layer 573 to ensure that separation occurs at the desired junction when the releasable portion 532 of rigidiying member 528 is lifted by means of tab 534. For example, the surface of the elastomeric member 515 which is secured to the rigidifying member 528 by adhesive layer 573 could be provided with a surface designed to easily release the adhesive layer when subjected to a peeling force without causing a significant portion of the adhesive to remain on the elastomeric member 515. This avoids irritation of the skin in the event the elastomeric member 515 is ultimately placed in contact therewith. Coatings or layers of non-irritating material could also be employed on elastomeric member 515 to ensure that these objectives are met.

Affixing a Pair of Composite Laminate Structures 510 to the Waistband of a Disposable Diaper 80

A composite laminate structure 510 was attached to each end portion 1 of the rear waistband of a disposable diaper 80 using the same general procedure as for the embodiments 210 of Example II. However, elements 235 and 236 (the polyethylene film layer and the segment of double-sided adhesive tape, respectively) used in Example II were not needed with the composite laminate structure embodiments 510 of Example V. The release papers (not shown) initially located on the uppermost surfaces of the double-sided adhesive tape strips 570 and 572 were removed from the entire top surface of composite laminate structure 510 and the composite laminate structure was first attached to the topsheet (lowermost) side 6 of end portion 1 of diaper 80, as generally illustrated in FIG. 5A. Portion 530 of the composite laminate structure 510 was thereafter folded over to affix the exposed adhesive surface to tape segment 572 to the backsheet (uppermost) side 5 of the diaper, as generally illustrated in FIG. 5B.

Alternatively, the application procedure could be reversed. Portion 530 of rigidifying member 528 could first be adhered to the backsheet (uppermost) side 5 of the first end portion 1 of disposable diaper 80 and the remainder of the composite laminate structure 510 could be folded over to contact the topsheet (lowermost) side 6 of the first end portion 1 of disposable diaper 80.

Whichever of the aforementioned application procedures is employed, the composite laminate structure 510 is ultimately connected to both surfaces of the diaper. This creates a force distributing Y-shaped yoke when the releasable portion 532 of rigidiying member 528 is separated from the prestretched and tensioned elastomeric meber 515 and affixed to end portion 2 of the article while subject to a relatively low degree of tension, $T_1$. This Y-shaped yoke is generally similar to that provided in the non-elasticized disposable diaper tape fastening system disclosed in commonly assigned U.S. Pat. No. 3,848,594 issued to Buell on Nov. 19, 1974 and hereby incorporated herein by reference.

The aforementioned diaper was applied to a baby model using the same general procedure as was used for the embodiments of Example II, and the same basic shirring of the first end portion of the article was observed, i.e., a multiplicity of gathers 523, 574 were formed on the backsheet (uppermost) side 5 and the topsheet (lowermost) side 6, respectively, of the first end portion 1 of the disposable diaper 80. As with the earlier embodiments, increasing the tension to a higher level, $T_2$, as shown in FIG. 5D, reduced the amplitude of the gathers 523, 574 in the first end portion of the diaper.

As will be appreciated by those skilled in the art, many of the materials utilized to fabricate most of the composite laminate structures described in the present specification, including composite laminate structure 510, can be obtained in roll, or at least bulk, form which will permit them to be fed continuously as a web. Accordingly, the material which is selected for elastomeric member 515 is preferably one which can be subjected to cross-machine direction stretching or tentering as it is fed to an assembly station. Since cross-directional stretching will normally cause a degree of machine direction foreshortening, the elastomeric material can simultaneously be subjected to a degree of machine direction stretching so that upon removal of the cross-machine direction tension, the amount of machine direction distortion is minimized. Once secured to rigidifying member 528, the elastomer may be released from the tentering mechanism, as it will be held in a prestretched and tensioned condition by the rigidifying member 528.

The resultant composite laminate structure 510 can, if desired, be rewound in roll form, with or without a layer of release paper to protect the exposed adhesive. For example, the nonadhesive containing surface of rigidifying member 528 could be provided with a surface designed to release the adhesive material with which it comes in contact when wound into a roll. This could be accomplished by surface treatment, lamination of a release surface or other means well known in the art. This roll stock may be fed continuously in the machine direction along with a continuously moving diaper web and cut into discrete segments at the time of transfer onto the diaper web, each of the discrete segments having the configuration generally shown in FIG. 5A.

As will also be appreciated by those skilled in the art, the same basic procedures may be employed to create continuous rolls of nearly any of the composite laminate structures described in the present specification, provided the cross-section of the composite laminate structure is substantially uniform along its depth. The composite laminate structure 510 is particularly preferred because of its similarity to the Y-shaped tape fastener system disclosed in the aforementioned commonly assigned U.S. Pat. No. 3,848,594 to Buell.

The composite structures 510 can be applied to the body-contacting surface of the moving diaper web such that portion 530 of the rigidifying member extends laterally beyond the edge of the diaper web so that it can thereafter be plowed over and affixed to the backsheet (uppermost) surface 5 of the diaper web, as generally shown in FIG. 5B.

Figure 5C:
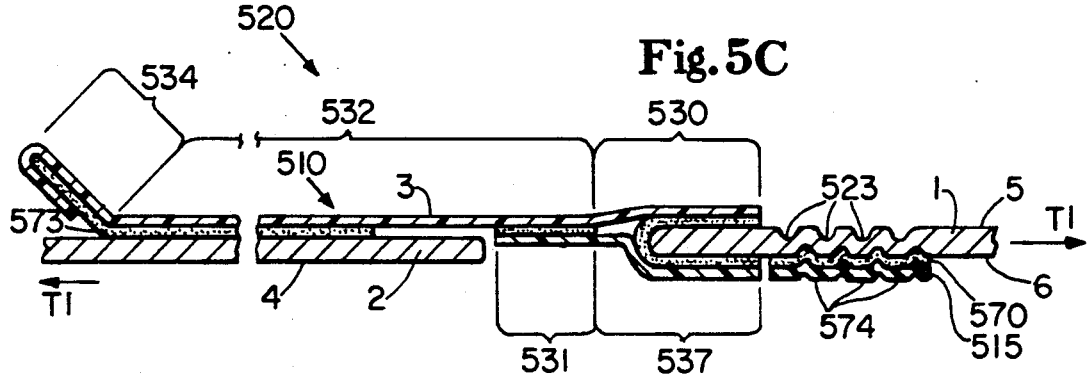
FIG. 5C is a cross-sectional illustration of the first and second end portions of the article to which the composite laminate structure shown in FIGS. 5 and 5A has been affixed after the releasable portion of the rigidifying member has been separated from the prestretched and tensioned elastomeric member and affixed tgo the uppermost surface of the second end portion of the article while subject to a relatively low degree of tension, $T_1$.
Figure 5D:
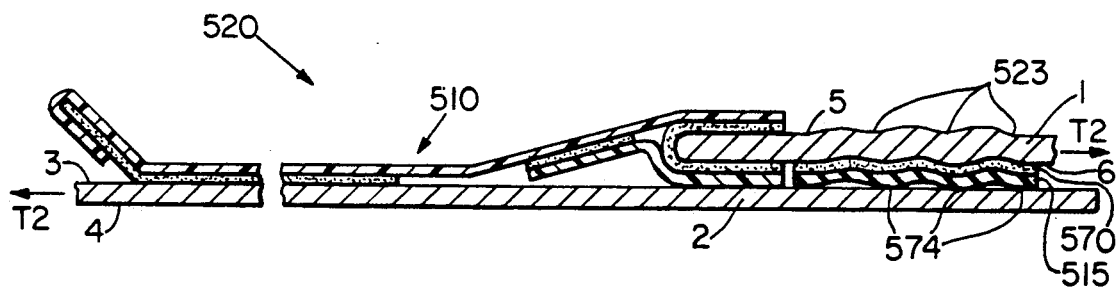
FIG. 5D is a cross-sectional illustration of the article shown in FIG. 5B after the releasable end portion of the rigidifying member of the composite laminate structure has been affixed to the uppermost surface of the second end portion of the article while subject to a much higher degree of tension, $T_2$.

When the resultant fastening system embodiment 520 is activated by pulling on lift tab 534, tension is released in the cross-machine direction, i.e., in a direction generally parallel to the diaper waistband, as shown in FIG. 5C. Thus, in a particularly preferred embodiment, the present invention permits continuous, high-speed application of elastomeric members which have been prestretched and tensioned in the cross-machine direction to a continuously moving web without the need to control the stretched elastic during the application process. Separation of the rigidifying member from the prestretched elastomeric member of members causes automatic shirring of the article in the cross-machine direction without the need to apply heat or any other type of stimulus required with most prior art cross-machine direction elasticization systems.

It is recognized that the present invention is not limited to the use of double-sided pressure sensitive adhesive tapes, as described in connection with embodiment 510 shown in FIG. 5. For example, single-sided pressure sensitive adhesive tapes could be employed for members 528 and 538 in a configuration of the type generally disclosed in the aforementioned commonly assigned U.S. Pat. No. 3,848,594 to Buell, thereby eliminating the need for double-sided adhesive strips 531, 570, 571, 572 and 573. It is further recognized that the present invention is in no way limited to the use of pressure sensitive adhesive tapes. Any material or combination of materials having suitable, and preferably releasable, securement characteristics may be employed with equal facility, e.g., Velcro ® materials and the like. Alternatively, adjustable interlocking bayonet and sheath arrangements such as those used to close trash bags could be employed. The use of pressure sensitive adhesive tapes, particularly double-sided pressure sensitive adhesive tapes, to construct many of the exemplary embodiments described herein is merely to facilitate a clear understanding of how the present invention may be practiced to advantage.

EXAMPLE VI

Consumer Activated Elasticized Tape Tab with Post-Application Activation

Figure 6:
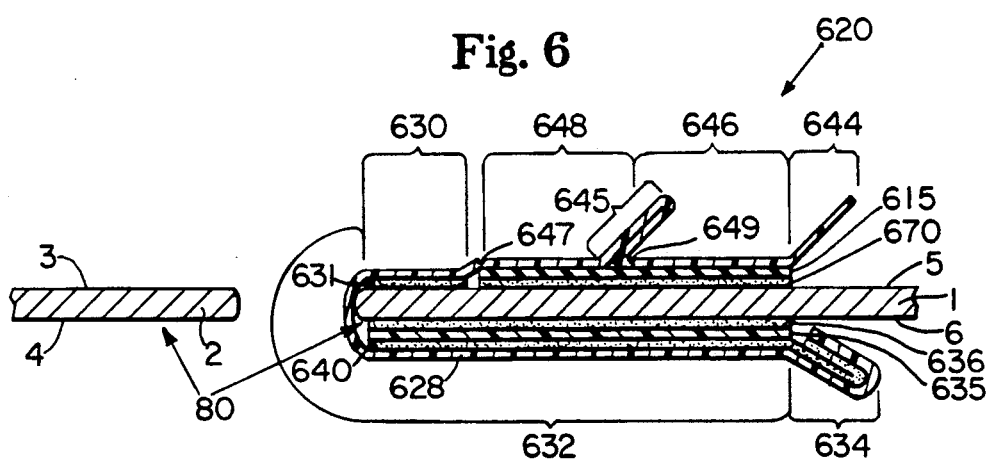
FIG. 6 is a cross-sectional illustration of the first and second end portions of another article of the present invention, said article being somewhat similar to those shown in FIGS. 1-5, but including two removable rigidifying members which can be independently removed from the composite laminate structure after the first and second end portions of the article have been secured to one another.

The elasticized fastening system embodiment 620 schematically depicted in the cross-section of FIG. 6 is a hypothetical example. It can be constructed utilizing essentially the same materials as were used to construct most of the other exemplary embodiments described earlier herein. It is preferably secured to the first end portion 1 of a disposable diaper waistband 80 in the manner generally disclosed in FIG. 6. It differs from the earlier embodiments in that it employs a fastening member 628 comprising a fixed portion 630, removable portion 632 and a lift tab 634. It also differs from earlier embodiments in that separation of the releasable portion 632 of the fastening member 628 from the topsheet (lowermost) surface 6 of the first end portion of the diaper does not automatically release the tension in the prestretched elastomeric member 615.

Immediately adjacent the fixed portion 630 of the fastening member 628 there is provided a stress concentrating notch 647. The elastomeric member 615, which is located to the right of stress concentrating notch 647 in FIG. 6, is held in a prestretched and tensioned condition by a pair of removable rigidifying members 646, 648 which include a pair of lift tabs 644, 645, respectively. As can be seen from FIG. 6, fastening member 628 and rigidifying members 646, 648 preferably comprise opposing ends of a single element and are separated from one another by means of stress concentrating notch 647. Intermediate the first and second removable rigidifying members 646 and 648 there is provided an additional stress concentrating notch 649 to permit the pair of rigidifying members to be removed independently of one another. The lowermost surface of the rigidifying members 646, 648 is preferably secured to the elastomeric member 615 while the elastomeric member 615 is in a prestretched and tensioned condition using heat and pressure, as generally described in connection with fastening system embodiment 120 of Example I. The lowermost surface of the prestretched and tensioned elastomeric member 615 preferbly includes a section of double-sided adhesive tape 670 which secures the prestretched and tensioned elastomeric member to the backsheet (uppermost) side 5 of the end portion 1 of the disposable diaper waistband 80.

The fixed portion 630 of the fastening member 628 is preferably secured to the backsheet (uppermost) side 5 of the first end portion 1 of the diaper by means of a bond 631 formed using either Dow 355 Medical Adhesive or another section of double-sided adhesive tape.

A layer of polyethylene film 635 is preferably secured to the topsheet (lowermost) side 6 of the first end portion 1 of the disposable diaper waistband 80, also by means of a section of double-sided adhesive tape 636. Another section of double-sided adhesive tape 640 is preferably secured to the releasable portion 632 of the fastening member 628. The free end of the releasable portion of the fastening member is folded upon itself to form a lift tab 634, as generally shown in FIG. 6. The exposed surface of the section of double-sided adhesive tape 640 temporarily adheres the releasable portion 632 of the fastening member 628 to the layer of polyethylene film 635 on the topsheet (lowermost) side 6 of the first end portion of the diaper waistband.

Figure 6A:
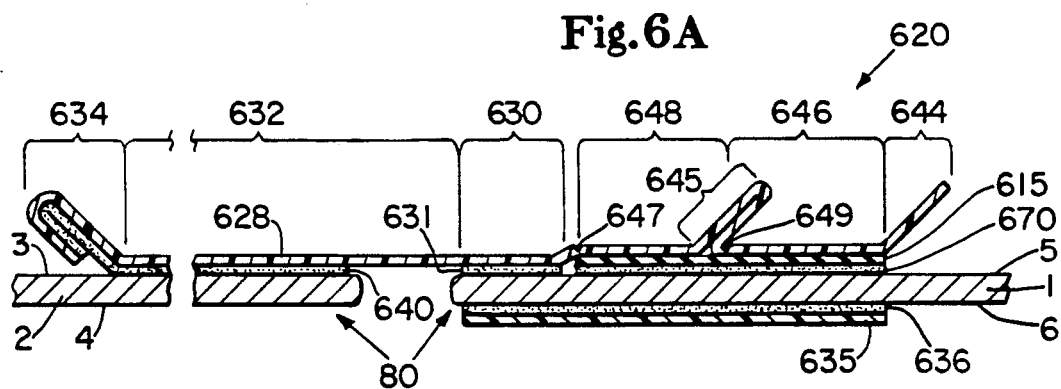
FIG. 6A shows the condition which exists when the first and second end portions of the article shown in FIG. 6 are secured to one another in an untensioned condition prior to separation of any portion of the rigidifying member from the prestretched and tensioned elastomeric member.

FIG. 6A illustrates the condition which would exist when the releasable portion 632 of the fastening member 628 is removed from the topsheet (lowermost) side 6 of the first end portion of the diaper wasitband and affixed to the backsheet (uppermost) side 3 of the second end portion 2 of the disposable diaper waistband 80. Because the pair of removable rigidifying members 646 and 648 remain undisturbed, tension is still maintained in the prestretched elastomeric member 615.

Figure 6B:
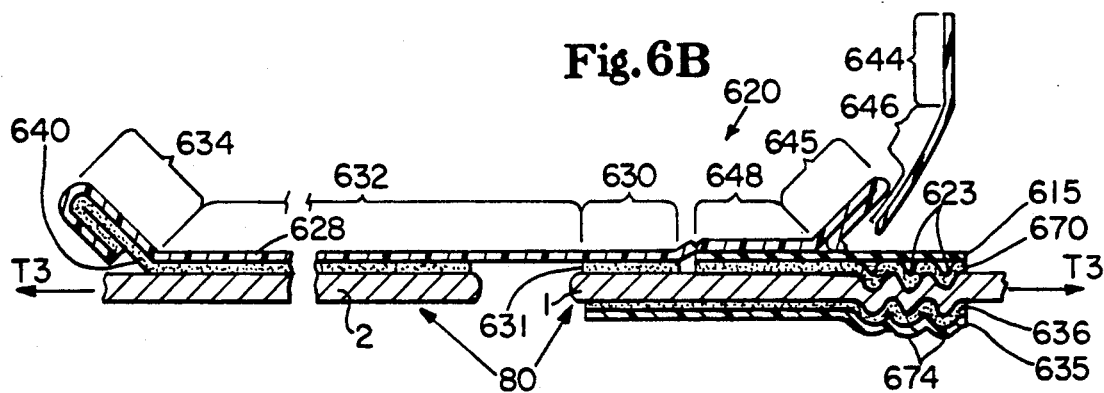
FIG. 6B is an illustration of the end portions of the article shown in FIG. 6A after the first removable rigidifying member has been separated from the corresponding protion of the prestretched and tensioned elastomeric member so as to introduce a degree of shirring in the first end portion of the article and a relatively low degree of tension, $T_3$, into the opposed end portions of the article.

FIG. 6B illustrates the condition which would exist when the first removable rigidifying member 646 is stripped and separated from the remainder of the structure by means of lift tab 644 and stress concentrating notch 649. Gathers 623, 674 are formed in the first end portion of the article by that portion of the prestretched elastomeric member 615 in which the tension has, at least to a degree, been released. This produces an initial degree of tension, $T_3$, in the opposing end portions of the diaper waistband.

Figure 6C:
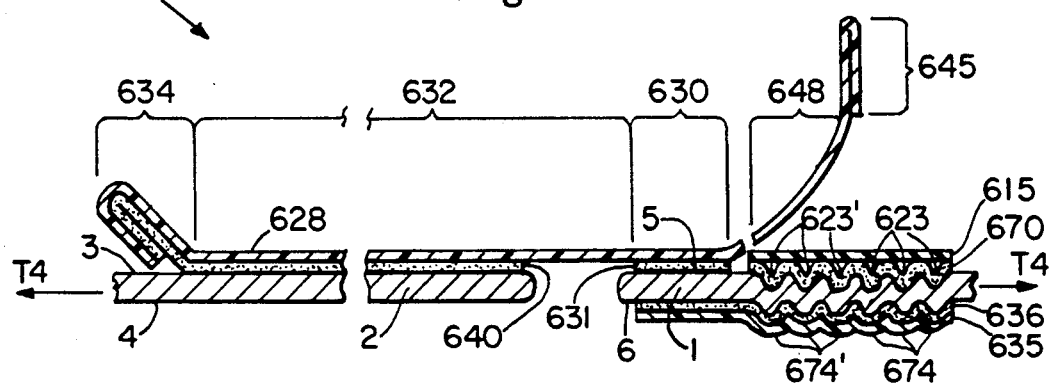
FIG. 6C is a cross-sectional illustration of the article shown in FIG. 6B after the second removable regidifying member has been separated from the prestretched and tensioned elastomeric member, so as to produce further shirring of the first end portion of the article and a higher degree of tension, $T_4$, in the opposed end portions of the article.

FIG. 6C illustrates the condition which would exist when the second removable rigidifying member 648 is stripped and separated from the remainder of the structure by means of lift tab 645 and stress concentrating notch 647. Additional gathers 623', 674' are formed in the first end portion of the article and a new, higher level of tension, $T_4$, is established in the opposing end portions of the diaper waistband.

As will be appreciated by those skilled in the art, the elasticized fastening system embodiment 620 illustrated in FIGS. 6 through 6C offers considerable flexibility as to when activation shall occur. It may, if desired, be activated entirely by the manufacturer of the article, partially by the manufacturer of the article and partially by the end user of the article or entirely by the end user of the article.

Figure 6D:
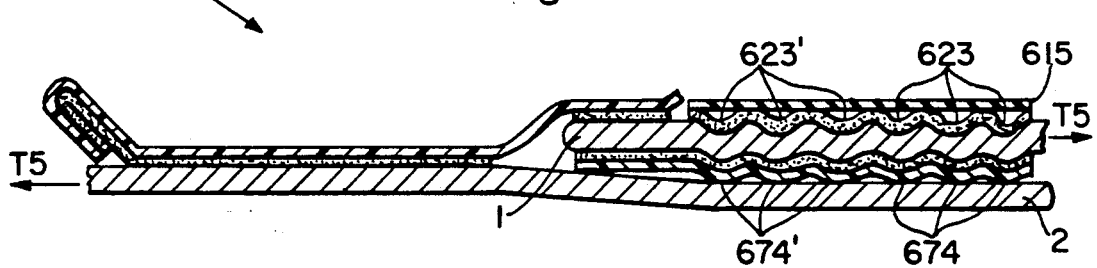
FIG. 6D is a cross-sectional illustraiton of the article shown in FIG. 6C after the opposed end portions of the article have been temporarily disconnected from one another and resecured in overlapping relation while subject to a new and higher degree of tension, $T_5$.

FIG. 6D illustrates the condition which would exist if the fastening system embodiment 620 shown in FIG. 6C were temporarily disconnected and subjected to a new and greater level of tension, $T_5$, at the time the releasable portion 632 of the fastening member 628 is re-secured in overlapping relation to the backsheet (uppermost) side 3 of the second end portion of the diaper waistband. Note that the amplitude of gathers 623, 623', 674, 674' generally decreases as the level of tension in the opposing end portions of the article increases. Also note that after stripping away of both removable rigidifying members 646, 648 the size and frequency of gathers 623 and 623' should be approximately the same, as should the size and frequency of gathers 674 and 674'. This is due to the tension equalization which occurs about the entire waistband of the installed diaper.

EXAMPLE VII

Consumer Activated Elasticized Tape Tab with Post-Application Activation

Figure 7:
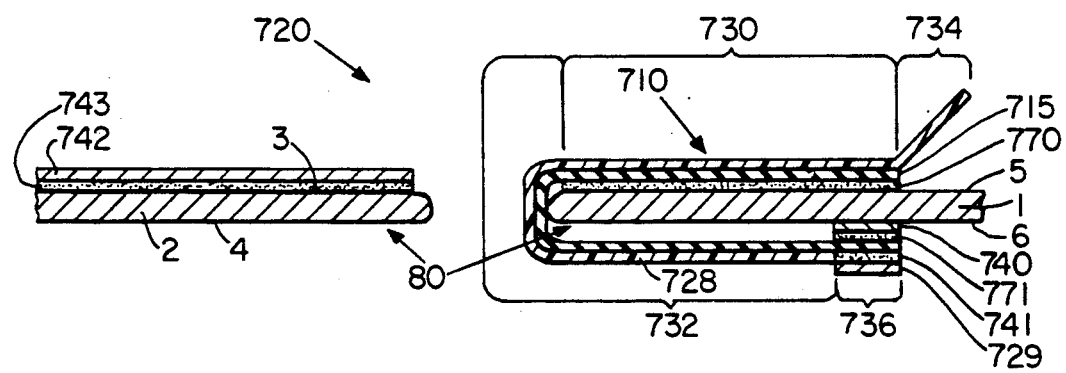
FIG. 7 is a cross-sectional illustration of the first and second end portions of another article of the present invention, said article being somewhat similar to those shown in FIGS. 1-6, but employing a rigidifying member which can be separated from the prestretched and tensioned elastomeric member after the first and second end portions of the article have been secured to one another, the elastomeric member serving not only to shirr the first end portion of said article, but also to elastically connect said first and second end portions of said article to one another, said article being shown prior to securement of its opposing end portions to one another.

The elasticized fastening system embodiment 720 schematically depicted in the cross-section of FIG. 7 includes at least one prestretched and tensioned elastomeric member 715 that is not activated until after the releasable portion 732 of rigidifying member 728 has been anchored to the second end portion 2 of the waistband of disposable diaper 80 by the user. It differs from many of the earlier embodiments in that the rigidifying member 728 does not remain with the fastening system once the tension in the fastening system has been released. It differs from all of the exemplary embodiments specifically described earlier herein in that the illustrated fastening system embodiment 720 does not use double-sided adhesive tape to secure the two end portions of the disposable diaper 80 together. Finally, it is the only disclosed embodiment which not only elastically shirrs the first end portion of the article to be elastically shirred, but in addition connects the first and second end portions of the article to one another via the elastomeric member.

Tension is preferably released in fastening system embodiment 720 after the diaper end portions are secured to one another by separating the entire rigidifying member 728 from the composite laminate structure 710 and discarding it. This is accomplished by pulling on lift tab 734. If the tension initially applied by the user is greater than the tension initially provided in the prestretched elastomeric member or members, removal of rigidifying member 728 will allow the waistband to expand and thereby lessen the degree of tension present. If, on the other hand, the tension initially applied by the user is less than the tension initially provided in the prestretched elastomeric member or members 715, removal of rigidifying member 728 will contract the waistband and thereby increase the degree of tension present.

Additional Material Used to Construct Composite Laminate Structure 710

Velcro ® —hook 740 and loop 742 fastening material, as avialable from Velcro USA Inc., Manchester, N.H.

Construction Procedure for the Composite Laminate Structure 710

The same general procedure that was used to construct the Example II composite laminate structure embodiments 210 was also used in constructing the Example VII composite laminate structure embodiments 710. The differences are noted throughout the description hereinafter set forth.

The pair of Dritz elastomeric members 715 (#4141 as in Example I) were secured to the rigidifying member 728 while prestretched and tensioned using the Vertrod sealer at a heat setting of approximately 165° Fahrenheit (74° Centigrade) and a gauge pressure setting of 30 pounds per square inch. The elastomeric members 715 were in parallel alignment and spaced approximately ⅛" apart. Both the elastomeric members 715 and the rigidifying member 728 were longer than those used in making the exemplary embodiments described earlier herein.

Double-sided adhesive tape 770 was applied to the lowermost surface of that portion of prestretched and tensioned elastomeric members 715 located directly under fixed portion 730 of rigidifying member 728, i.e., that portion which remains fixed to the first end portion 1 of the waistband of disposable diaper 80 as the releasable portion 732 is being secured to the second end portion 2 of the waistband of disposable diaper 80.

The rigidifying member was provided with a lift tab 734 located adjacent the fixed portion 730 of rigidifying member 728. An untensioned portion of elastomeric members 715 extended beyond the free end of the releasable portion 732 of rigidifying member 728. The untensioned portion of elastomeric members 715 was fitted with a small section of the hook-containing Velco ® material 740 using Dow 355 Medical Adhesive on both surfaces to create bond 771, as generally shown in FIG. 7. Directly opposite this Velcro ® material 740 a small discrete section of Pet-G material 729 was attached to the opposite surface of the untensioned ends of the pair of elastomeric members 715 using double-sided adhesive tape 741 to form a fastening tab 736 at the free end of releasable portion 732 of rigidifying member 728. The hook-containing Velcro ® 740 on fastening tab 736 of the composite laminate structure 710 functions to secure the free end of the elastomeric members 715 to the topsheet (lowermost) side 6 of the diaper prior to activation. It also functions after activation to secure the free end of the elastomeric members 715 to the loop-containing Velcro ® 742, which is secured to the backsheet (uppermost) side 3 of the second end portion 2 of the diaper waistband by means of double-sided adhesive tape 743.

Affixing a Pair of Composite Laminate Structures 710 to the Waistband of a Disposable Diaper 80

One of the previously described composite laminate structures 710 was applied to the backsheet (uppermost) side 5 of each end portion 1 of the rear waistband of a disposable diaper 80 using the exposed surface of double-sided adhesive tape 770, as generally shown in FIG. 7. After the portion of the composite laminate structure 710 coinciding with fixed portion 730 of rigidifying member 728 was attached to the backsheet (uppermost) surface 5 of end portion 1, the releasable extension of the composite laminate structure, i.e., that portion coinciding with releasable portion 732 of rigidifying member 728 was folded around the edge of the diaper end portion 1, and the fastening tab 736 having the hook-containing Velcro ® material 740 was temporarily secured in place by engaging it with the nonwoven topsheet located on the lowermost side 6 of the diaper 80, as generally illustrated in FIG. 7. This corresponds to the normal position of composite laminate structure 710 prior to its being placed in service by the end user.

To provide a receiving surface for the hook-containing Velcro ® material 740, two sections of mating loop-containing Velcro ® material 742 were attached to the backsheet (uppermost) side 3 of each second end portion 2 of diaper 80 using double-sided adhesive tape 743.

The resultant disposable diaper was installed on a baby model using the same general procedure used to apply the exemplary disposable diapers described earlier herein. The releasable extension of the composite laminate structure, i.e., that portion coinciding with releasable portion 732 of rigidifying member 728 which included the hook-containing Velcro ® material 740, was separated from the topsheet (lowermost) side 6 of each end portion 1 of diaper 80 and attached to the mating loop-containing Velcro ® material 742 on the backsheet (uppermost) side 3 of the corresponding end portion 2 of diaper 80, as generally illustrated in FIG. 7A.

Figure 7A:
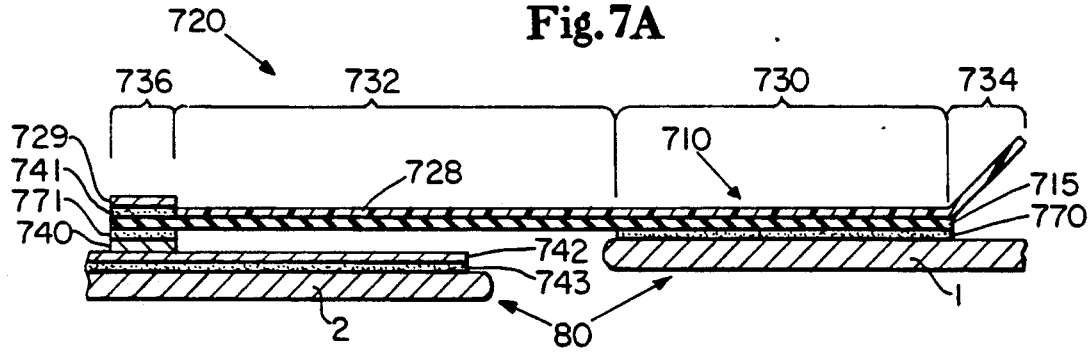
FIG. 7A is a cross-sectional illustration of the article shown in FIG. 7 after the first and second end portions of the article have been secured to one another in a substantially untensioned state, said cross-section illustrating the condition which exists prior to separation of the rigidifying member from the prestretched and tensioned elastomeric member.
Figure 7B:
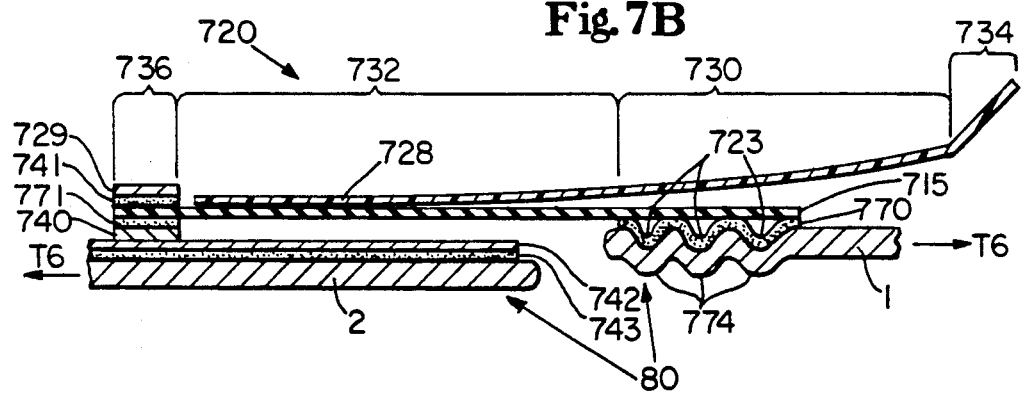
FIG. 7B is a cross-sectional illustration of the article shown in FIG. 7A after the rigidifying member has been completely separated from the prestretched and tensioned elastomeric member, thereby introducing a degree of shirring in the first end portion of the article and a degree of tension, $T_6$, in the opposing end portions of the article.

For purposes of clarity, no tension is present in end portions 1 and 2 when the diaper 80 is in the condition illustrated in FIG. 7A. At this point there is also no effective elasticity imparted by the prestretched and tensioned elastomeric members 715. Elasticity is imparted only when the rigidifying member 728 is removed by pulling on lift tab 734 and stripping the Pet-G film comprising rigidifying member 728 from the prestretched and tensioned elastomeric members 715. When the rigidifying member 728 is removed, the prestretched elastomeric members 715 attempt to return to their original untensioned condition along their length, thereby introducing a degree of tension, $T_6$, into end portions 1 and 2, as generally shown in FIG. 7B. This introduces article shirring comprising gathers 723, 774 into diaper end portion 1 as that portion of the elastomeric members 715 originally coinciding with the fixed portion 730 of rigidifying member 728 contracts. In addition, end portions 1 and 2 move closer toward one another as that portion of the prestretched and tensioned elastomeric members 715 originally coinciding with releasable portion 732 of rigidifying member 728 contracts.

FIG. 7B illustrates the condition which exists when diaper end portion 1 and diaper end portion 2 are subject to a relatively low degree of tension, $T_6$ introduced solely by stripping away rigidifying member 728.

Figure 7C:
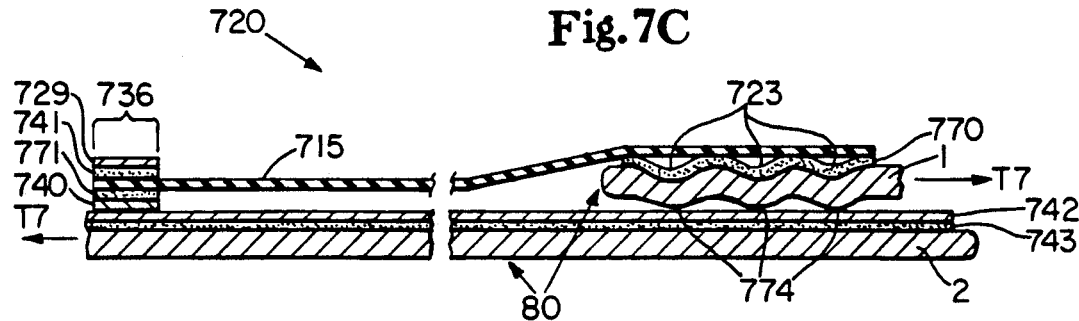
FIG. 7C illustrates the condition which would exist if the end portions of the article shown in FIG. 7B were temporarily disconnected fron one another and resecured in overlapping relation while subject to a higher degree of tension, $T_7$.

FIG. 7C depicts the condition which would exist if a greater degree of tension, $T_7$, were applied to the diaper waistband at the time the end portions 1 and 2 were secured together and the rigidifying member 728 were thereafter separated from the composite laminate structure 710. The amplitude of the gathers 723, 724 is reduced and there is a greater degree of stretching in that portion of elastomeric members 715 originally coinciding with the releasable portion 732 of rigidifying member 728.

As with previously described exemplary embodiments, the degree of article shirring, i.e., the amplitude and frequency of gathers 723, 724 will vary inversely as the tension in the waistband is varied. However, unlike many of the previously described exemplary embodiments, the final tension which results in the assembled diaper waistband will usually be different than the tension applied by the user during the joinder process. This is due to the fact that the elastomeric members 715 are maintained in a fully tensioned condition until after end portions 1 and 2 of the diaper have been secured to one another by the user.

In elasticized fastening system embodiment 720 the final tension in the assembled diaper waistband is directly influenced by the degree of prestretching introduced into the elastomeric members 715 during fabrication of the laminate structure 710. Removal of rigidifying member 728 from composite laminate structure 710 after the first and second end portions of the diaper have been secured to one another will permit the waistband to expand beyond the original size fixed by the user in those situations where the tension initially applied by the user exceeds the tension initially provided in the prestretched elastomeric members 715. In this instance, the portion of elastomeric members 715 originally coinciding with the releasable portion 732 of rigidifying member 728 will undergo further stretching.

Conversely, if the tension initially provided in the prestretched elastomeric members 715 is greater than the tension initially applied by the user when the first and second end portions of the diaper are secured to one another, the waistband will contract and increase the level of tension in the waistband. In the latter instance, both the portion of elastomeric members 715 originally coinciding with the releasable portion 732 of rigidifying member 728 and the portion of elastomeric members 715 originally coinciding with the fixed portion 730 of rigidifying member 72, will contract causing the end portions of the article to move closer toward one another and the first end portion of the article to shirr.

EXAMPLE VIII

Consumer Activated Elasticized Tape Tab with Post-Application Activation

Figure 8:
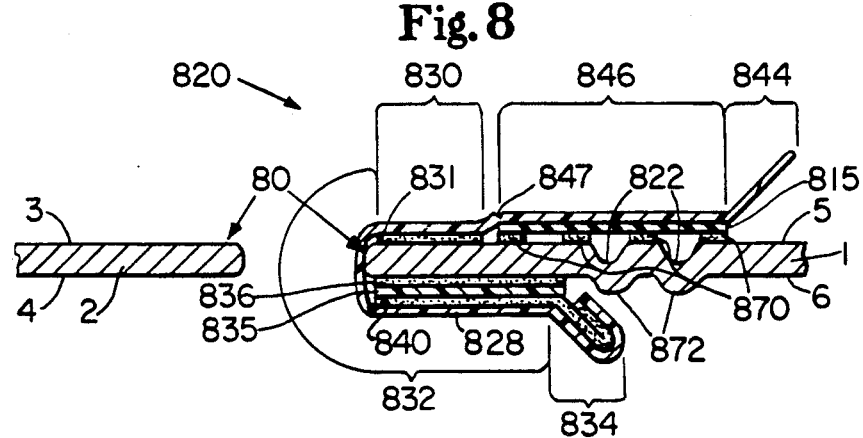
FIG. 8 is a cross-sectional illustration of the first and second end portions of still another article of the present invention prior to securement of the first and second end portions of the article to one another, a portion of the prestretched and tensioned elastomeric member in the composite laminate structure being secured to a substantially planar section of the first end portion of the article and a portion of the prestretched and tensioned elastomeric member being secured to a pregathered section of the first end portion of the article.

The elasticized fastening system embodiment 820 schematically depicted in the cross-section in FIG. 8 is a hypothetical example. In many respects it is similar to hypothetical embodiment 620 shown in FIG. 6. However, it employs only a single removable rigidifying member rather than a pair of removable rigidifying members, as used in embodiment 620.

Elasticized fastening system embodiment 820 may be constructed utilizing the same basic procedures utilized to construct embodiment 620. The same materials of construction may also be employed. The same materials of construction may also be employed. The chief difference between embodiment 820 and embodiment 620 is that the prestretched and tensioned elastomeric member 815 is secured to the backsheet (uppermost) side 5 of the first end portion 1 of disposable diaper waistband 80 by means of a multiplicity of discrete, spaced apart segments of double-sided adhesive tape 870 rather than a single continuous segment. In addition, part of the first end portion 1 of the diaper 80 is foreshortened by means of gathers 822, 872 prior to securement of the prestretched and tensioned elastomeric member 815 to the backsheet (uppermost) side 5 of the diaper waistband. This produces an elasticized fastening system 820 having the configuration generally shown in FIG. 8.

As with embodiment 620, fastening system embodiment 820 employs a fastening member 828 comprising a fixed portion 830, a removable portion 832 and a lift tab 834. Like embodiment 620, separation of the releasable portion 832 of the fastening member 828 from the topsheet (lowermost) side 6 of the first end portion of the diaper does not automatically release the tension in the prestretched elastomeric member 815.

In the illustrated fastening system embodiment 820, releasable portion 832 of fastening member 828 corresponds generally to releasable portion 632 of fastening member 628 in embodiment 620; fixed portion 830 of fastening member 828 corresponds generally to fixed portion 630 of fastening member 628; bond 831 which secures fixed portion 830 of fastening member 828 to the backsheet (uppermost) side 5 of the first end portion 1 of the diaper corresponds to bond 631; layer of polyethylene film 835 which is secured to the topsheet (lowermost) side 6 of the first end portion 1 of the disposable diaper waistband 80 by means of a section of double-sided adhesive tape 836 corresponds to layer of polyethylene film 635 and section of double-sided adhesive tape 636, respectively; section of double-sided adhesive tape 840 which is secured to the releasable portion 832 of fastening member 838 corresponds to section of double-sided adhesive tape 640; stress concentrating notch 847 corresponds generally to stress concentrating notch 647; removable rigidifying member 846 corresponds generally to removable rigidifying member 646 and lift tab 844 corresponds generally to lift tab 644. As with embodiment 620, fastening member 828 and rigidifying member 846 preferably comprise opposing ends of a single element and are separated from one another by means of stress concentrating notch 847.

Figure 8A:
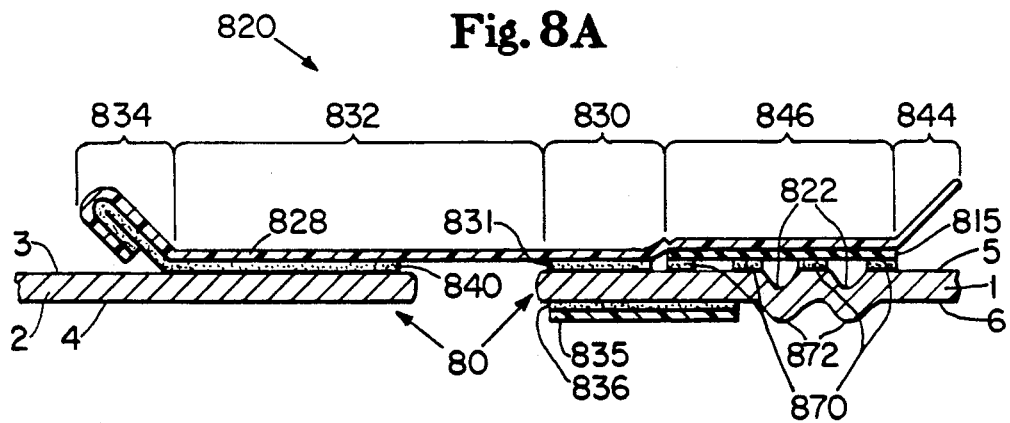
FIG. 8A is a cross-sectional illustration of the article shown in FIG. 8 after the first and second end portions of the article have been secured to one another in a substantially untensioned condition, said composite structure being shown prior to separation of the rigidifying member from the prestretched and tensioned elastomeric member.

When the releasable portion 832 of the fastening member is secured to the backsheet (uppermost) side 3 of the second end portion 2 of the diaper waistband in a substantially untensioned condition, as generally shown in FIG. 8A, there is still no release of tension in prestretched elastomeric member 815.

Figure 8B:
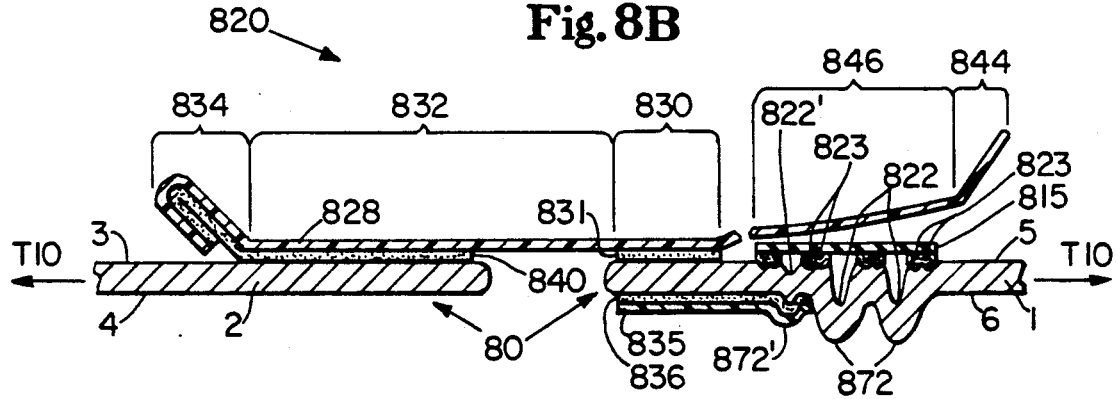
FIG. 8B illustrates the condition of the article shown in FIG. 8A after the removable rigidifying member has been completely separated from the prestretched and tensioned elastomeric member, thereby producing two different degrees of article shirring in the first end portion of the article as well as introducing a degree of tension, $T_{10}$, into the opposed end portions of the article.

However, when the removable rigidifying member 846 is stripped and separated from the remainder of the structure by means of lift tab 844 and stress concentrating notch 847, the condition generally illustrated in FIG. 8B arises. In particular, the amplitude of gathers 822, 872 is increased due to a partial release of tension in the prestretched and tensioned elastomeric member 815. Smaller gathers 822', 872' are formed in those areas corresponding to the initially nongathered portion of the first end portion of the article. In addition, fine scale gathers 823 are formed in the areas where adhesive sections 870 are secured to elastomeric member 815. As a result, an initial level of tension, $T_{10}$, is established in the opposing end portions 1, 2 of the disposable diaper waistband 80.

FIG. 8C is generally similar to FIG. 8A with the exception that the first and second end portions of the diaper waistband are secured to one another in overlapping relation while subject to a much higher level of tension, $T_{11}$, which is greater than the amount of tension initially present in the prestretched and tensioned elastomeric member 815. When this condition exists, stripping and separating removable rigidifying member 846 from the remainder of the structure has the effect of decreasing the level of tension in the opposed end portions of the article to a new lower level, $T_{12}$, which is less than the initial level of tension, $T_{11}$. As can be seen from FIG. 8D, the prestretched and tensioned elastomeric member 815 actually undergoes a degree of elongation rather than a degree of contraction when this situation arises. This phenomenon is further evidenced by the fact that gathers 822, 872 will exhibit lower amplitudes and frequencies than were initially present when the elasticized fastening system embodiment 820 was constructed. In addition, fine scale gathers 823 do not appear, since the tensioned elastomeric member 815 undergoes further elongation rather than contraction upon separation of removable rigidifying member 846 from the remainder of the structure.

Thus, preferred elasticized fastening system embodiments of the present invention may adjust tension either upwardly or downwardly, relative to the degree of tension initially established in the opposing end portions of the article by the end user.

Figure 9:
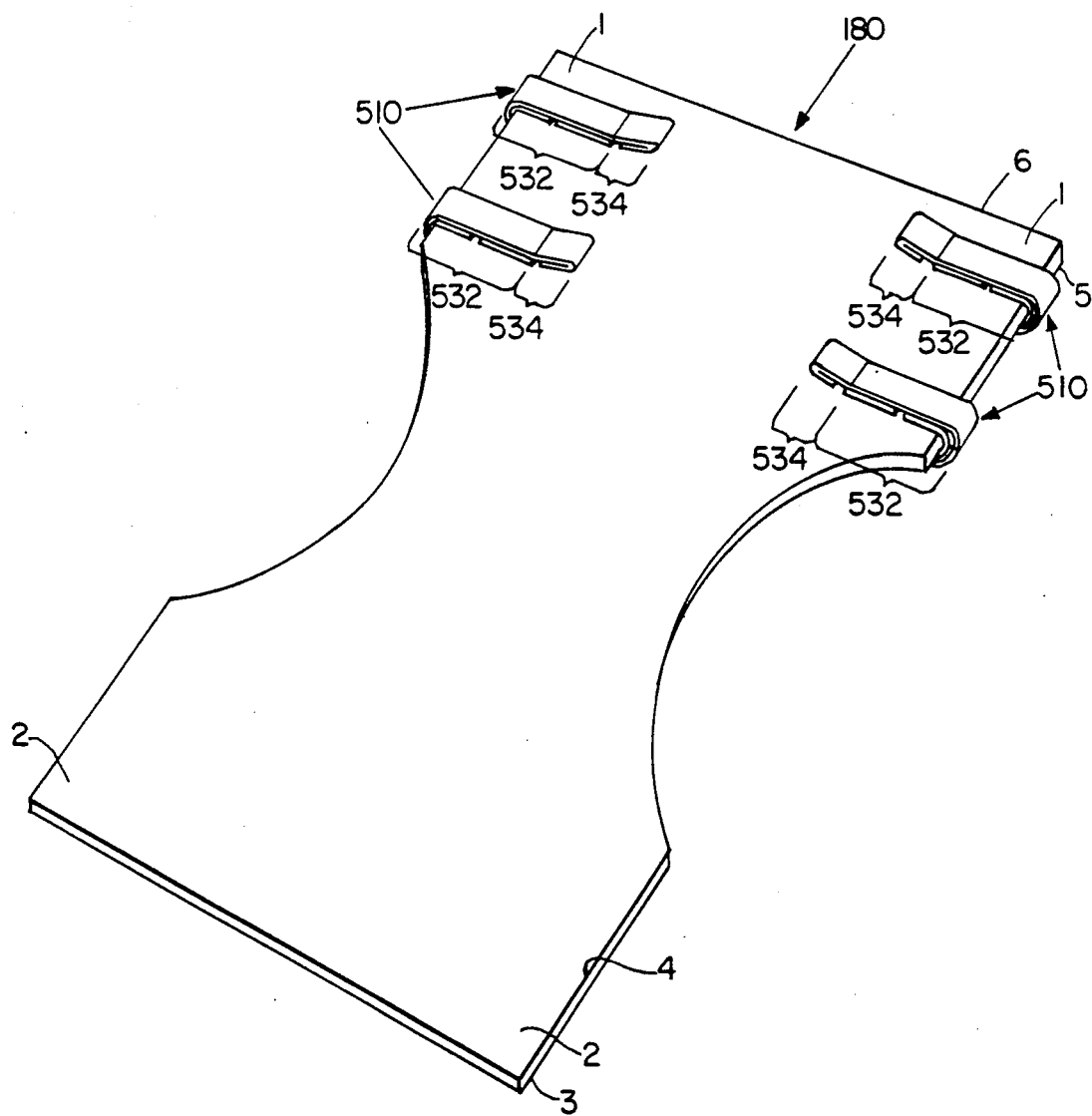
FIG. 9 is a simplified perspective illustration of a disposable diaper employing a pair of opposed waitband fasteners of the type generally illustrated in FIG. 5 and a pair of opposed legband fasteners, also of the type generally illustrated in FIG. 5.

The Disposable Diaper Embodiment of FIG. 9

In FIG. 9 there is shown a simplified perspective view of a hypothetical disposable diaper 180, generally similar to diaper embodiment 80 described earlier herein, said diaper also having a rear waistband with a pair of opposing end portions 1 and a front waistband with a pair of opposing end portions 2.

The hypothetical diaper embodiment 180 illustrated prior to installation in FIG. 9 includes four composite laminate structure embodiments 510 of the type generally described in connection with EXAMPLE V. Two of these composite laminate structure embodiments are secured in the waistband area of the diaper and two are secured at the leg openings of the diaper.

Figure 10:
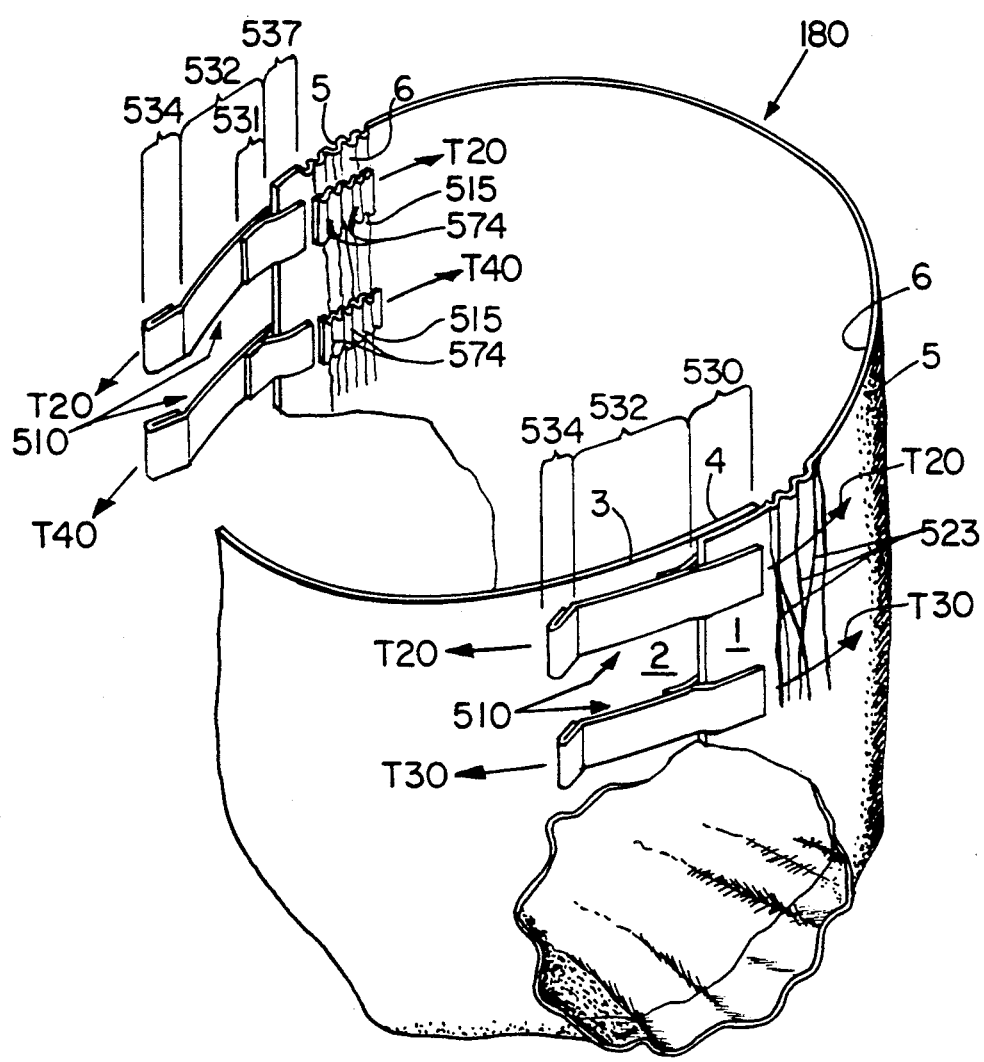
FIG. 10 is a simplified, partially segmented, perspective illustration of the diaper of FIG. 9 showing the conditions which would exist after the diaper has been applied about the waist of an infant (not shown) while subject to a waistband tension $T_{20}$ and legband tensions $T_{30}$ and $T_{40}$.

FIG. 10 is a partially segmented perspective view of the diaper 180 shown in FIG. 9 as it would appear after it has been affixed about the waist and legs of a wearer (not shown). In particular, the diaper has been assembled so that its topsheet side 6, 4 resides on the interior of the structure, while its backsheet side 5, 3 resides on the outside of the diaper. The releasable portions 532 of the composite laminate structure embodiments 510 in the waistband area have been stripped away and affixed to the corresponding second end portions 2 of the diaper waistband. This establishes a degree of shirring in each first end portion of the diaper waistband, as generally shown in FIG. 10, and a degree of tension, $T_{20}$, in the waistband of the assembled diaper. (This of course assumes that the garment has been secured about the body of a wearer, not shown.)

In similar fashion, a composite laminate structure 510 has been utilized to elastically close each opening of the diaper about one of the wearer's legs (not shown) and establish a separate and independent level of tension, $T_{30}$, $T_{40}$, in the respective leg openings of the assembled diaper 180. As pointed out earlier in the present specification, the levels of tensions, $T_{30}$, $T_{40}$, can be adjusted independently of one another as well as independently of the level of tension, $T_{20}$, established in the waistband portion of the diaper. Thus the fit of each opening in the assembled diaper 180 can be precisely adjusted to the desired level of tension by the user during the application process. As will be appreciated by those skilled in the art, elasticized fastening systems of the present invention may be utilized either in addition to or in lieu of other elasticized features extending partially or completely about the legband and/or waistband openings of the assembled diaper.

When the elasticity is provided solely in the areas shown in FIG. 10, those portions of the diaper which are most subject to leakage, i.e., the central portions of the front and back waistband opening and the lowermost portion of the leg openings are substantially free of gathers. This can be of benefit from a leakage standpoint, since the elastic gathers normally formed by continuous elastic waistbands and legbands can sometimes permit fluid leakage through the gathers, particularly when the applied tensions are low enough that a continuous seal is not formed against the wearer's skin in these areas. A possible secondary benefit of fastening systems of the type illustrated in FIG. 10 is that the releasable portions of the rigidifying members are normally easier to find and grasp, since the tension in the elastomeric members is not released until after the consumer has already grasped them and initiated the installation procedure.

As with the earlier described embodiments of the present invention, the waistband tension, $T_{20}$, and/or the leg band tensions, $T_{30}$, $T_{40}$, can, of course, be readjusted as desired by temporarily disconnecting the first and second end portions of the assembled diaper from one another and resecuring them to one another at whatever tension level is desired.

While particular embodiments of the present invention have been illustrated and described, it would be obvious to those skilled in the art that various changes and modifications can be made without departing from the spirit and scope of the present invention. It is intended to cover in the appended claims, all such modifications that are within the scope of this invention.

What is claimed is:

1. An article having a pliable portion which is to be applied about the periphery of a member having a substantially predetermined cross-section so as to encircle said member and elastically secured in place, said pliable encircling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable portion of said segment including an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon said prestretched and tensioned elastomeric member, said rigidifying member having a fixed portion permanently secured to said first end portion of said pliable encircling portion of said article and a releasable portion which can be separated from said first end portion, said releasable portion of said rigidifying member further including means for securing it to said second end portion of said pliable encircling portion of said article, whereby separating the releasable portion of said rigidifying member from said first end portion releases the tensile forces in said composite structure to produce a degree of shirring in said segment in the direction of prestretching of said elastomeric member, the degree of shirring in the secured article being inversely proportional to the amount of tension applied to the pliable encircling portion of said article when its first and second end portions are secured to one another.

2. The article of claim 1, wherein said prestretched and tensioned elastomeric member and said rigidifying member which form said composite structure are secured in fixed relation to one another by means of a bond having high shear strength and low peel strength, said bond being formed by the application of heat and pressure to opposing surfaces of said members.

3. The article of claim 1, wherein said means for securing said releasable portion of said rigidifying member to said second end portion of said pliable encircling portion of said article comprises a pressure sensitive adhesive on one of its surfaces.

4. The article of claim 1, wherein said means for securing said releasable portion of said rigidifying member to said second end portion of said pliable encircling portion of said article comprises a two-component mechanically engaging system having a male element secured to one of said releasable portion of said rigidifying member or said second end portion of said pliable encircling portion of said article and a complementary female element secured to the other of said releasable portion of said rigidifying member or said second end portion of said pliable encircling portion of said article.

5. The article of claim 1, wherein said releasable portion of said rigidifying member further includes a free end having a lift tab to facilitate easy grasping of said releasable portion of said rigidifying member to initiate the article securement process.

6. The article of claim 1, wherein said fixed portion of said rigidifying member and said releasable portion of said rigidifying member are secured to the same surface of said article when said first and second end portions of said pliable encircling portion of said article are elastically secured to one another.

7. The article of claim 1, wherein said fixed portion of said rigidifying member, said releasable portion of said rigidifying member and said prestretched and tensioned elastomeric member are all located on the same surface of said first end portion of said pliable encircling portion of said article prior to separation of said releasable portion of said rigidifying member from said first end portion.

8. The article of claim 7, wherein said prestretched and tensioned elastomeric member is continuously secured to said first end portion of said pliable encircling portion of said article along its entire length.

9. The article of claim 8, wherein said prestretched and tensioned elastomeric member is secured to said first end portion of said pliable encircling portion of said article by means of a pressure sensitive adhesive.

10. The article of claim 1, wherein said article comprises a disposable diaper and wherein said pliable encircling portion of said article comprises opposing waistband portions of said disposable diaper.

11. The article of claim 1, wherein said article comprises a disposable diaper and wherein said pliable encircling portion of said article comprises opposing legband portions of said diaper.

12. The article of claim 1, further including a secondary rigidifying member which, prior to separation from said first end portion of said pliable encircling portion of said article, maintains only a portion of said prestretched elastomeric member in its tensioned condition, whereby said secondary rigidifying member can be separated from said first end portion of said pliable encircling portion of said article to release the tension in the corresponding portion of said prestretched elastomeric member without releasing the tension in the balance of said prestretched and tensioned elastomeric member.

13. The article of claim 12, wherein said secondary rigidifying member comprises a portion of manufacturing apparatus used to assemble said composite structure comprising said prestretched and tensioned elastomeric member and said rigidifying member.

14. The article of claim 12, wherein said secondary rigidifying member comprises a portion of manufacturing apparatus used to affix said composite structure to said article.

15. The article of claim 13 or claim 14, wherein said portion of said manufacturing apparatus comprising said secondary rigidifying member is a conveyor belt.

16. The article of claim 1, wherein said releasable portion of said rigidifying member is secured in fixed relation to one surface of said first end portion of said pliable encircling portion of said article and said prestretched and tensioned elastomeric member is secured in fixed relation to an opposite surface of the first end portion prior to securement of said first and second end portions of said pliable encircling portion of said article to one another, whereby resistance to the tensile forces present in said prestretched elastomeric member is transmitted from the releasable portion of said rigidifying member to said prestretched elastomeric member through said first end portion of said pliable encircling portion of said article.

17. The article of claim 16, wherein said article comprises a disposable diaper and wherein said pliable encircling portion of said article comprises opposing waistband portions of said disposable diaper.

18. The article of claim 1, wherein said fixed portion of said rigidifying member is secured to a first surface of said first end portion of said pliable encircling portion of said article and said releasable portion of said rigidifying member is secured to on opposed second surface of said first end portion, said article further including a secondary securement member attached to said second surface of said first end portion as well as to said releasable portion of said rigidifying member in an area immediately adjacent on edge of said first end portion, whereby tensile forces imposed upon said releasable portion of said rigidifying member during securement of said first and second end portions of said pliable encircling portion of said article to one another are transmitted to both said first and second surfaces of said first end portion.

19. The article of claim 18, wherein said article comprises a disposable diaper having a backsheet on said first surface and a topsheet on said second surface and wherein said fixed portion of said rigidifying member is secured to said first surface of said diaper and said secondary securement member is secured to said second surface of said diaper.

20. The article of claim 19, wherein said rigidifying member and said secondary securement member comprise pressure sensitive adhesive tape and wherein the adhesive surfaces of said releasable portion of said rigidifying member and the portion of said secondary securement member in contact therewith in an area immediately adjacent the edge of said first end portion of said pliable encircling portion of said diaper are in face-to-face engagement with one another.

21. The article of claim 20, wherein said releasable portion of said rigidifying member further includes a free end having a lift tab to facilitate easy grasping of said releasable portion of said rigidifying member to initiate the article securement process.

22. The article of claim 20, wherein the same pressure sensitive adhesive on said releasable portion of said rigidifying member which secures said releasable portion of said rigidifying member in fixed relation to said prestretched and tensioned elastomeric member prior to separation of said releasable portion said rigidifying member from said first end portion of said pliable encircling portion of said article also secures said second end portion of said pliable encircling portion of said article to said first end portion when said first and second end portions are elastically secured to one another.

23. The article of claim 22, wherein said prestretched and tensioned elastomeric member is further provided with a release surface which permits easy peeling of said releasable portion of said rigidifying member from said first end portion of said pliable encircling portion of said article.

24. The article of claim 23, wherein said release surface comprises a layer of release material secured to said prestretched and tensioned elastomeric member.

25. An article having a pliable portion which is to be applied about the periphery of a member having a substantially predetermined cross-section so as to substantially encircle said member and elastically secured in place, said pliable encricling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable segment including an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon said prestretched and tensioned elastomeric member, said first end portion of said pliable encircling portion of said article further including a fastening member, said fastening member having a fixed portion permanently secured to said first end portion and a releasable portion which initially coincides at least to a degree with said prestretched and tensioned elastomeric member in said elastically shirrable segment in said first end portion of said article but which can be separated from said first end portion, said releasable portion of said fastening member further including means for securing it to said second end portion of said pliable encircling portion of said article, whereby said releasable portion of said fastening member can be separated from said first end portion and secured to said second end portion without releasing the tensile forces in said composite structure and said at least one rigidifying member can thereafter be separated from said composite structure to produce a degree of shirring in said segment in the direction of prestretching of said elastomeric member, the degree of shirring in the elastically secured article being inversely proportional to the amount of tension applied to the pliable encircling portion of said article when its first and second end portions are secured to one another.

26. An article having a pliable portion which is to be applied about the periphery of a member having a substantially predetermined cross-section so as to substantially encircle said member and elastically secured in place, said pliable encircling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable segment including an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon sid prestretched and tensioned elastomeric member, said first end portion of said pliable encircling portion of said article further including a fastening member, said fastening member and said rigidifying member comprising opposing ends of a single element, said fastening member having a fixed portion permanently secured to said first end portion and a releasable portion which can be separated from said first end portion, said releasable portion of said fastening member further including means for securing it to said second end portion of said pliable encircling portion of said article, whereby said releasable portion of said fastening member can be separated from said first end portion and secured to said second end portion without releasing the tensile forces in said composite structure and said at least one rigidifying member can thereafter be separated from said compositive structure to produce a degree of shirring in said segment in the direction of prestretching of said elastomeric member, the degree of shirring in the elastically secured article being inversely proportional to the amount of tension applied to the pliable encircling portion of said article when its first and second end portions are secured to one another.

27. The article of claim 25 or claim 26, wherein said first end portion of said pliable encircling portion of said article is extensible in a direction parallel to the direction of said tension in said composite structure immediately prior to its securement to said article, whereby said rigidifying member in said composite structure not only functions to maintain said prestretched elastomeric member in said composite structure in tension after it has been secured to said article, but also to prevent extension of said first end portion of said pliable encircling portion of said article if said first end portion is subjected to externally applied tension prior to separation of said rigidifying member from said prestretched elastomeric member.

28. An article having a pliable portion which is to be applied about the periphery of a member having a substantially predetermined cross-section so as to substantially encircle said member and elastically secured in place, said pliable encircling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable segment inlcuding an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon said prestretched and tensioned elastomeric member, said first end portion of said pliable encircling portion of said article further including a fastening member, said fastening member having a fixed portion permanently secured to said first end portion and a releasable portion which can be separated from said first end portion, said releasable portion of said fastening member further including means for securing it to said second end portion of said pliable encircling portion of said article, the overall length of said first end portion of said pliable encircling portion of said article to which said composite structure is secured being greater than the overall length of the prestretched and tensioned elastomeric member in said composite structure even prior to separation of said rigidifying member from said prestretched elastomeric member so that said first end portion to which said composite structure is secured is extensible in a direction parallel to the direction of said tension in said composite structure immediately prior to its securement to said article and so that said first end portion to which said composite structure is secured exhibits a shirred appearance even prior to separation of said rigidifying member from said prestretched elastomeric member in said composite structure, whereby said releasable portion of said fastening member can be separated from said first end portion and secured to said second end portion without releasing the tensile forces in said composite structure and said at least one rigidifying member can thereafter be separated from said composite structure to produce a degree of shirring in said segment in the direction of prestretching of said elastomeric member, the degree of shirring in the elastically secured article being inversely proportional to the amount of tension applied to the pliable encircling portion of said article when its first and second end portions are secured to one another.

29. An article having a pliable portion which is to be applied about the periphery of a member having a substantially predetermined cross-section so as to substantially encircle said member and elastically secured in place, said pliable encircling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable segment including an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon said prestretched and tensioned elastomeric member, said first end portion of said pliable encircling portion of said article further including a fastening member, said fastening member and said rigidifying member comprising opposing ends of a single element, said fastening member having a fixed portion permanently secured to said first end portion and a releasable portion which can be separated from said first end portion, said releasable portion of said fastening member further including means for securing it to said second end portion of said pliable encircling portion of said article, the overall length of said first end portion of said pliable encircling portion of said article to which said composite structure is secured being greater than the overall length of the prestretched and tensioned elastomeric member in said composite structure even piror to separation of said rigidifying member from said prestretched elastomeric member so that said first end portion to which said composite structure is secured is extensible in a direction parallel to the direction of said tension in said composite structure immediately prior to its securement to said article and so that said first end portion to which said composite structure is secured exhibits a shirred appearance even prior to separation of said rigidifying member from said prestretched elastomeric member in said composite structure, whereby said releasable portion of said fastening member can be separated from said first end portion and secured to said second end portion without releasing the tensile forces in said composite structure and said at least one rigidifying member can thereafter be separated from said composite structure to produce a degree of shirring in said segment in the direction of prestretching of said elastomeric member, the degree of shirring in the elastically secured article being inversely proportional to the amount of tension applied to the pliable encircling portion of said article when its first and second end portions are secured to one another.

30. The article of claim 25, including at least two rigidifying members secured in fixed relation to and along the length of said prestretched and tensioned elastomeric member, whereby said rigidifying members can be separated from said composite structure independently from one another to independently release the tension in the corresponding portion of the prestretched elastomeric member.

31. An article having a pliable portion which is to be applied about the periphery of a member having a substantially predetermined cross-section so as to substantially encircle said member and elastically secured in place, said pliable encircling portion of said article having a first end portion and a second end portion which are to be secured to one another after said pliable encircling portion of said article has been applied about the periphery of said member, said first end portion including at least one segment which is capable of being elastically shirred along at least a portion of its length, said shirrable segment including an elastomeric member which, prior to securement of said first and second end portions of said pliable encircling portion of said article to one another, is maintained in a prestretched and tensioned condition in the desired direction of shirring, the opposed ends of said shirrable segment being interconnected to one another through said prestretched and tensioned elastomeric member, said prestretched and tensioned elastomeric member also being secured in fixed relation to at least one rigidifying member to form a composite structure which is strong enough to resist collapse in a direction parallel to the tensile forces acting upon said prestretched and tensioned elastomeric member, said composite structure further including a releasable extension temporarily secured to said first end portion of said pliable encircling portion of said article, said releasable extension of said composite structure further including means for securing it to said second end portion of said pliable encircling portion of said article, whereby said releasable extension of said composite structure can be separated from said first end portion and secured to said second end portion without releasing the tensile forces in any portion of said composite structure, thereby permitting said rigidifying member to thereafter be separated from said composite structure to release the tension in the corresponding portion of said prestretched elastomeric member and to produce a degree of shirring in said segment in the direction of prestretching of said elastomeric member, the degree of shirring in the elastically secured article being inversely proportional to the amount of tension applied to the pliable encircling portion of said article when its first and second end portions are secured to one another.

32. The article of claim 31, wherein said means for securing said releasable extension of said composite structure to said second end portion of said pliable encircling portion of said article comprises a pressure sensitive adhesive tape.

33. The article of claim 31, wherein said means for securing said releasable extension of said composite structure to said second end portion of said pliable encircling portion of said article comprises a pair of mechanically entangling members, one of which is located on said releasable extension of said composite structure and the other which is located on said second end portion.

* * * * *

UNITED STATES PATENT AND TRADEMARK OFFICE
CERTIFICATE OF CORRECTION

PATENT NO. : 5,092,862
DATED : March 3, 1992
INVENTOR(S) : DELMAR R. MUCKENFUHS and STEVEN R. GILBERT It is certified that error appears in the above-identified patent and that said Letters Patent is hereby corrected as shown below:

Column 6, line 2, insert after "respect" -- to --.
Column 7, line 55, "tgo" should read -- to --.
Column 8, line 60, "fron" should read -- from --.
Column 9, line 41, "waitband" should read -- waistband --.
Column 16, line 3, "incorporatig" should read -- incorporating --.
Column 16, line 30, "Me." should read -- MI. --.
Column 17, line 21, "gnerally" should read -- generally --.
Column 17, line 47, "double-sides" should read -- double-sided --.
Column 19, line 9, "owermost" should read -- lowermost --.
Column 26, line 6, "(1N2732as" should read -- (1N2732) as --.
Column 26, line 56, "rigidiying" should read -- rigidifying --.
Column 27, line 20, "to", second occurrence, should read -- of --.
Column 27, line 35, "rigidiying" should read -- rigidifying --.
Column 27, line 37, "meber" should read -- member --.
Column 28, line 51, "of" should read -- or --.
Column 29, line 53, "preferbly" should read -- preferably --.
Column 33, line 28, "724" should read -- 774 --.
Column 33, line 35, "724" should read -- 774 --.
Column 34, line 2, "72," should read -- 728 --.

UNITED STATES PATENT AND TRADEMARK OFFICE
CERTIFICATE OF CORRECTION

PATENT NO. : 5,092,862
DATED : March 3, 1992
INVENTOR(S) : DELMAR R. MUCKENFUHS and STEVEN R. GILBERT It is certified that error appears in the above-identified patent and that said Letters Patent is hereby corrected as shown below:

Column 34, lines 20-21, delete "The same materials of construction may also be employed. --.

Column 34, line 59, "838" should read -- 828 --.

Column 36, line 20, "tensions," should read -- tension, --.

Column 39, line 7, Claim 18, "on" should read -- an --.

Column 39, line 12, Claim 18, "on" should read -- an --.

Column 39, line 45, Claim 22, after "portion" insert -- of --.

Column 40, line 63, Claim 26, "sid" should read -- said --.

Column 41, line 11, Claim 26, "compositive" should read -- composite --.

Column 19, line 43, "sicne" should read -- since --.

Signed and Sealed this

Tenth Day of August, 1993

Attest:

MICHAEL K. KIRK

Attesting Officer    Acting Commissioner of Patents and Trademarks